(12) United States Patent
Chegini et al.

(10) Patent No.: US 10,786,330 B2
(45) Date of Patent: *Sep. 29, 2020

(54) PROXIMAL-END SECUREMENT OF A MINIMALLY INVASIVE WORKING CHANNEL

(71) Applicant: MEDOS INTERNATIONAL SARL, Le Locle (CH)

(72) Inventors: Salman Chegini, Bern (CH); Joern Richter, Kandern (DE); Daniel Thommen, Liestal (CH); Peter Senn, Waldenburg (CH)

(73) Assignee: Medos International Sarl, Le Locle (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/156,022

(22) Filed: Oct. 10, 2018

(65) Prior Publication Data

US 2019/0110860 A1 Apr. 18, 2019

Related U.S. Application Data

(63) Continuation of application No. 14/546,620, filed on Nov. 18, 2014, now Pat. No. 10,111,712, which is a
(Continued)

(51) Int. Cl.
*A61B 17/34* (2006.01)
*A61F 2/46* (2006.01)
(Continued)

(52) U.S. Cl.
CPC .......... *A61B 90/50* (2016.02); *A61B 17/3403* (2013.01); *A61B 17/3421* (2013.01);
(Continued)

(58) Field of Classification Search
CPC . A61B 17/02; A61B 17/0206; A61B 17/0218; A61B 17/0293; A61B 17/3403;
(Continued)

(56) References Cited

U.S. PATENT DOCUMENTS 2,697,433 A 12/1954 Zehnder
3,135,263 A 6/1964 Connelley
(Continued)

FOREIGN PATENT DOCUMENTS

CN 102727309 B 11/2014
DE 9415039 U1 11/1994
(Continued)

OTHER PUBLICATIONS

U.S. Appl. No. 14/481,822, filed Sep. 9, 2014, Proximal-End Securement of a Minimally Invasive Working Channel.
(Continued)

*Primary Examiner* — Kevin T Truong
*Assistant Examiner* — Tracy L Kamikawa
(74) *Attorney, Agent, or Firm* — Nutter McClennen & Fish LLP

(57) ABSTRACT

The present invention is directed at minimally invasive systems in which the proximal end portion of the working channel has either zero or a limited range of movement in the lateral direction. A first embodiment has a slidable collar attached to a pair of flanges, wherein movement of the collar is bounded by an annular frame. A second embodiment has a substantially spherical element attached to the tube. A third embodiment has a plurality of caps. A fourth embodiment is adapted for a larger working channel.

17 Claims, 20 Drawing Sheets

Related U.S. Application Data continuation-in-part of application No. 14/481,822, filed on Sep. 9, 2014, now Pat. No. 9,924,979.

(51) Int. Cl.
  *A61B 90/50* (2016.01)
  *A61B 17/00* (2006.01)

(52) U.S. Cl.
  CPC ...... *A61B 17/3423* (2013.01); *A61B 17/3468* (2013.01); *A61F 2/4601* (2013.01); *A61F 2/4603* (2013.01); *A61B 2017/00261* (2013.01); *A61B 2017/3405* (2013.01); *A61B 2017/3492* (2013.01)

(58) Field of Classification Search
  CPC ............ A61B 17/3415; A61B 17/3417; A61B 17/3421; A61B 17/3423; A61B 17/3462; A61B 17/3468; A61B 17/3472; A61B 17/171; A61B 17/1717; A61B 17/1757; A61B 17/1742; A61B 17/1746; A61B 17/1778; A61B 2017/3405; A61B 2017/3407; A61B 2017/3425; A61B 2017/3427; A61B 2017/3441; A61B 2017/3443; A61B 2017/3445; A61B 2017/3456; A61B 2017/347; A61B 2017/348; A61B 17/3492; A61B 17/00261; A61B 1/32; A61F 2/4601; A61F 2/4603; A61F 2/4611; A61F 2002/4635
  See application file for complete search history.

(56) References Cited

U.S. PATENT DOCUMENTS

| | | | |
|---|---|---|---|
| RE32,021 E | 11/1985 | Scott, Jr. | |
| 4,573,448 A | 3/1986 | Kambin | |
| 4,646,738 A | 3/1987 | Trott | |
| 4,678,459 A | 7/1987 | Onik et al. | |
| 4,863,430 A | 9/1989 | Klyce et al. | |
| 4,888,146 A | 12/1989 | Dandeneau | |
| 5,080,662 A | 1/1992 | Paul | |
| 5,195,541 A | 3/1993 | Obenchain | |
| 5,213,567 A | 5/1993 | Masaki | |
| 5,285,795 A | 2/1994 | Ryan et al. | |
| 5,395,317 A | 3/1995 | Kambin | |
| 5,439,464 A | 8/1995 | Shapiro | |
| 5,529,580 A | 6/1996 | Kusunoki et al. | |
| 5,540,706 A | 7/1996 | Aust et al. | |
| 5,569,290 A | 10/1996 | McAfee | |
| 5,591,187 A | 1/1997 | Dekel | |
| 5,601,569 A | 2/1997 | Pisharodi | |
| 5,662,300 A | 9/1997 | Michelson | |
| 5,688,222 A | 11/1997 | Hluchy et al. | |
| 5,695,500 A | 12/1997 | Taylor et al. | |
| 5,730,754 A | 3/1998 | Obenchain | |
| 5,733,242 A | 3/1998 | Rayburn et al. | |
| 5,735,792 A | 4/1998 | Vanden Hoek et al. | |
| 5,820,623 A | 10/1998 | Ng | |
| 5,885,300 A | 3/1999 | Tokuhashi et al. | |
| 5,894,369 A | 4/1999 | Akiba et al. | |
| 5,899,425 A | 5/1999 | Corey, Jr. et al. | |
| 5,954,635 A | 9/1999 | Foley et al. | |
| 6,007,486 A | 12/1999 | Hunt et al. | |
| 6,033,105 A | 3/2000 | Barker et al. | |
| 6,053,907 A | 4/2000 | Zirps | |
| 6,063,021 A | 5/2000 | Hossain et al. | |
| 6,110,182 A | 8/2000 | Mowlai-Ashtiani | |
| 6,200,322 B1 | 3/2001 | Branch et al. | |
| 6,234,961 B1 | 5/2001 | Gray | |
| 6,283,966 B1 | 9/2001 | Houfburg | |
| 6,286,179 B1 | 9/2001 | Byrne | |
| 6,296,644 B1 | 10/2001 | Saurat et al. | |
| 6,322,498 B1 | 11/2001 | Gravenstein et al. | |
| 6,354,992 B1 | 3/2002 | Kato | |
| 6,371,968 B1 | 4/2002 | Kogasaka et al. | |
| 6,383,191 B1 | 5/2002 | Zdeblick et al. | |
| 6,447,446 B1 | 9/2002 | Smith et al. | |
| 6,468,289 B1 | 10/2002 | Bonutti | |
| 6,558,407 B1 | 5/2003 | Ivanko et al. | |
| 6,575,899 B1 | 6/2003 | Foley et al. | |
| 6,579,281 B2 | 6/2003 | Palmer et al. | |
| 6,626,830 B1 | 9/2003 | Califiore et al. | |
| 6,648,915 B2 | 11/2003 | Sazy | |
| 6,676,597 B2 | 1/2004 | Guenst et al. | |
| 6,688,564 B2 | 2/2004 | Salvermoser et al. | |
| 6,758,809 B2 | 7/2004 | Briscoe et al. | |
| 6,808,505 B2 | 10/2004 | Kadan | |
| 6,887,198 B2 | 5/2005 | Phillips et al. | |
| 6,983,930 B1 | 1/2006 | La Mendola et al. | |
| 7,087,058 B2 | 8/2006 | Cragg | |
| 7,104,986 B2 | 9/2006 | Hovda et al. | |
| 7,137,949 B2 | 11/2006 | Scirica et al. | |
| 7,182,731 B2 | 2/2007 | Nguyen et al. | |
| 7,313,430 B2 | 12/2007 | Urquhart et al. | |
| 7,341,556 B2 | 3/2008 | Shalman | |
| 7,434,325 B2 | 10/2008 | Foley et al. | |
| 7,591,790 B2 | 9/2009 | Pflueger | |
| 7,594,888 B2 | 9/2009 | Raymond et al. | |
| 7,618,431 B2 | 11/2009 | Roehm, III et al. | |
| 7,636,596 B2 | 12/2009 | Solar | |
| 7,637,905 B2 | 12/2009 | Saadat et al. | |
| 7,641,659 B2 | 1/2010 | Emstad et al. | |
| 7,771,384 B2 | 8/2010 | Ravo | |
| 7,794,456 B2 | 9/2010 | Sharps et al. | |
| 7,811,303 B2 | 10/2010 | Fallin et al. | |
| 7,824,332 B2 * | 11/2010 | Fakhrai | A61B 17/0206 600/217 |
| 7,931,579 B2 | 4/2011 | Bertolero et al. | |
| 7,946,981 B1 | 5/2011 | Cubb | |
| 7,951,141 B2 | 5/2011 | Sharps et al. | |
| 7,959,564 B2 | 6/2011 | Ritland | |
| 7,988,623 B2 | 8/2011 | Pagliuca et al. | |
| 8,007,492 B2 | 8/2011 | DiPoto et al. | |
| 8,038,606 B2 | 10/2011 | Otawara | |
| 8,043,381 B2 | 10/2011 | Hestad et al. | |
| 8,062,218 B2 | 11/2011 | Sebastian et al. | |
| 8,092,464 B2 | 1/2012 | McKay | |
| 8,096,944 B2 | 1/2012 | Harrel | |
| 8,202,216 B2 | 6/2012 | Melkent et al. | |
| 8,236,006 B2 | 8/2012 | Hamada | |
| 8,333,690 B2 | 12/2012 | Ikeda | |
| 8,360,970 B2 | 1/2013 | Mangiardi | |
| 8,372,131 B2 | 2/2013 | Hestad et al. | |
| 8,382,048 B2 | 2/2013 | Nesper et al. | |
| 8,397,335 B2 | 3/2013 | Gordin et al. | |
| 8,435,174 B2 | 5/2013 | Cropper et al. | |
| 8,460,180 B1 | 6/2013 | Zarate et al. | |
| 8,460,186 B2 | 6/2013 | Ortiz et al. | |
| 8,460,310 B2 | 6/2013 | Stern | |
| 8,491,595 B2 * | 7/2013 | Volpi | A61B 17/1714 606/96 |
| 8,491,599 B2 | 7/2013 | Heilala et al. | |
| 8,518,087 B2 | 8/2013 | Lopez et al. | |
| 8,535,220 B2 | 9/2013 | Mondschein | |
| 8,556,809 B2 | 10/2013 | Vijayanagar | |
| 8,585,726 B2 | 11/2013 | Yoon et al. | |
| 8,602,979 B2 | 12/2013 | Kitano | |
| 8,622,894 B2 | 1/2014 | Banik et al. | |
| 8,636,655 B1 | 1/2014 | Childs | |
| 8,690,764 B2 | 4/2014 | Clark et al. | |
| 8,721,536 B2 | 5/2014 | Marino et al. | |
| 8,740,779 B2 | 6/2014 | Yoshida | |
| 8,784,421 B2 | 7/2014 | Carrison et al. | |
| 8,821,378 B2 | 9/2014 | Morgenstern Lopez et al. | |
| 8,834,507 B2 | 9/2014 | Mire et al. | |
| 8,845,734 B2 | 9/2014 | Weiman | |
| 8,852,242 B2 | 10/2014 | Morgenstern Lopez et al. | |
| 8,870,753 B2 | 10/2014 | Boulais et al. | |
| 8,870,756 B2 | 10/2014 | Maurice | |
| 8,876,712 B2 | 11/2014 | Yee et al. | |
| 8,894,573 B2 | 11/2014 | Loftus et al. | |

(56) References Cited

U.S. PATENT DOCUMENTS

| | | |
|---|---|---|
| 8,894,653 B2 | 11/2014 | Solsberg et al. |
| 8,926,502 B2 | 1/2015 | Levy et al. |
| 8,932,207 B2 | 1/2015 | Greenburg et al. |
| 8,932,360 B2 | 1/2015 | Womble et al. |
| 8,936,605 B2 | 1/2015 | Greenberg |
| 8,974,381 B1 | 3/2015 | Lovell et al. |
| 8,986,199 B2 | 3/2015 | Weisenburgh, II et al. |
| 8,992,580 B2 | 3/2015 | Bar et al. |
| 9,028,522 B1 | 5/2015 | Prado |
| 9,050,146 B2 | 6/2015 | Woolley et al. |
| 9,055,936 B2 | 6/2015 | Mire et al. |
| 9,072,431 B2 | 7/2015 | Adams et al. |
| 9,078,562 B2 | 7/2015 | Poll et al. |
| 9,131,948 B2 | 9/2015 | Fang et al. |
| 9,144,374 B2 | 9/2015 | Maurice, Jr. |
| 9,198,674 B2 | 12/2015 | Benson et al. |
| 9,211,059 B2 | 12/2015 | Drach et al. |
| 9,216,016 B2 | 12/2015 | Fiechter et al. |
| 9,216,125 B2 | 12/2015 | Sklar |
| 9,232,935 B2 | 1/2016 | Brand et al. |
| 9,247,997 B2 | 2/2016 | Stefanchik et al. |
| 9,265,491 B2 | 2/2016 | Lins et al. |
| 9,277,928 B2 | 3/2016 | Morgenstern Lopez |
| 9,307,972 B2 | 4/2016 | Lovell et al. |
| 9,320,419 B2 | 4/2016 | Kirma et al. |
| RE46,007 E | 5/2016 | Banik et al. |
| RE46,062 E | 7/2016 | James et al. |
| 9,386,971 B1 | 7/2016 | Casey et al. |
| 9,387,313 B2 | 7/2016 | Culbert et al. |
| 9,414,828 B2 | 8/2016 | Abidin et al. |
| 9,486,296 B2 | 11/2016 | Mire et al. |
| 9,492,194 B2 | 11/2016 | Morgenstern Lopez et al. |
| 9,510,853 B2 | 12/2016 | Aljuri et al. |
| 9,526,401 B2 | 12/2016 | Saadat et al. |
| 9,579,012 B2 | 2/2017 | Vazales et al. |
| 9,603,510 B2 | 3/2017 | Ammirati |
| 9,603,610 B2 | 3/2017 | Richter et al. |
| 9,610,007 B2 | 4/2017 | Kienzle et al. |
| 9,610,095 B2 | 4/2017 | To |
| 9,629,521 B2 | 4/2017 | Ratnakar |
| 9,655,605 B2 | 5/2017 | Serowski et al. |
| 9,655,639 B2 | 5/2017 | Mark |
| 9,668,643 B2 | 6/2017 | Kennedy, II et al. |
| 9,675,235 B2 | 6/2017 | Lieponis |
| 9,700,378 B2 | 7/2017 | Mowlai-Ashtiani |
| 9,706,905 B2 | 7/2017 | Levy |
| 9,924,979 B2 | 3/2018 | Chegini et al. |
| 10,111,712 B2 | 10/2018 | Chegini et al. |
| 10,264,959 B2 | 4/2019 | Chegini et al. |
| 2002/0022762 A1 | 2/2002 | Beane et al. |
| 2002/0042607 A1 | 4/2002 | Palmer et al. |
| 2002/0138020 A1 | 9/2002 | Pflueger |
| 2003/0083555 A1 | 5/2003 | Hunt et al. |
| 2003/0171744 A1 | 9/2003 | Leung et al. |
| 2003/0191474 A1 | 10/2003 | Cragg et al. |
| 2004/0122446 A1 | 6/2004 | Solar |
| 2004/0127992 A1 | 7/2004 | Serhan et al. |
| 2004/0143165 A1 | 7/2004 | Alleyne |
| 2005/0085692 A1 | 4/2005 | Kiehn et al. |
| 2005/0090848 A1 | 4/2005 | Adams |
| 2005/0187570 A1 | 8/2005 | Nguyen et al. |
| 2005/0256525 A1 | 11/2005 | Culbert et al. |
| 2006/0206118 A1 | 9/2006 | Kim et al. |
| 2007/0055259 A1 | 3/2007 | Norton et al. |
| 2007/0129634 A1 | 6/2007 | Hickey et al. |
| 2007/0149975 A1 | 6/2007 | Oliver et al. |
| 2007/0203396 A1 | 8/2007 | McCutcheon et al. |
| 2007/0225556 A1 | 9/2007 | Ortiz et al. |
| 2007/0260113 A1 | 11/2007 | Otawara |
| 2008/0015621 A1 | 1/2008 | Emanuel |
| 2008/0033251 A1 | 2/2008 | Araghi |
| 2008/0081951 A1 | 4/2008 | Frasier et al. |
| 2008/0188714 A1 | 8/2008 | McCaffrey |
| 2009/0018566 A1 | 1/2009 | Escudero et al. |
| 2009/0024158 A1 | 1/2009 | Viker |
| 2009/0062871 A1 | 3/2009 | Chin et al. |
| 2009/0105543 A1 | 4/2009 | Miller et al. |
| 2009/0156898 A1 | 6/2009 | Ichimura |
| 2009/0187080 A1 | 7/2009 | Seex |
| 2009/0240111 A1 | 9/2009 | Kessler et al. |
| 2009/0287061 A1 | 11/2009 | Feigenbaum et al. |
| 2009/0318765 A1 | 12/2009 | Torii |
| 2010/0004651 A1 | 1/2010 | Biyani |
| 2010/0022841 A1 | 1/2010 | Takahashi et al. |
| 2010/0076476 A1 | 3/2010 | To et al. |
| 2010/0114147 A1 | 5/2010 | Biyani |
| 2010/0151161 A1 | 6/2010 | Da Rolo |
| 2010/0161060 A1 | 6/2010 | Schaller et al. |
| 2010/0210916 A1 | 8/2010 | Hu et al. |
| 2010/0256446 A1 | 10/2010 | Raju |
| 2010/0280325 A1 | 11/2010 | Ibrahim et al. |
| 2010/0284580 A1 | 11/2010 | Ouyang et al. |
| 2010/0286477 A1 | 11/2010 | Ouyang et al. |
| 2010/0312053 A1 | 12/2010 | Larsen |
| 2011/0028791 A1 | 2/2011 | Marino et al. |
| 2011/0054507 A1 | 3/2011 | Batten et al. |
| 2011/0098706 A1 | 4/2011 | Mullaney |
| 2011/0106261 A1 | 5/2011 | Chin et al. |
| 2011/0125158 A1 | 5/2011 | Diwan et al. |
| 2011/0130634 A1 | 6/2011 | Solitario, Jr. et al. |
| 2011/0295070 A1 | 12/2011 | Yasunaga |
| 2011/0319941 A1 | 12/2011 | Bar et al. |
| 2012/0095296 A1 | 4/2012 | Trieu et al. |
| 2012/0101338 A1 | 4/2012 | O'Prey et al. |
| 2012/0209273 A1 | 8/2012 | Zaretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0298820 A1 | 11/2012 | Manolidis |
| 2012/0316400 A1 | 12/2012 | Vijayanagar |
| 2013/0103067 A1 | 4/2013 | Fabro et al. |
| 2013/0103103 A1 | 4/2013 | Mire et al. |
| 2013/0150670 A1 | 6/2013 | O'Prey et al. |
| 2013/0150674 A1 | 6/2013 | Haig et al. |
| 2013/0172676 A1 | 7/2013 | Levy et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2013/0325011 A1* | 12/2013 | Cleveland .......... A61B 17/0482 606/80 |
| 2014/0066940 A1 | 3/2014 | Fang et al. |
| 2014/0074170 A1 | 3/2014 | Mertens et al. |
| 2014/0142584 A1 | 5/2014 | Sweeney |
| 2014/0148647 A1 | 5/2014 | Okazaki |
| 2014/0180321 A1 | 6/2014 | Dias et al. |
| 2014/0194697 A1 | 7/2014 | Seex |
| 2014/0215736 A1 | 8/2014 | Gomez et al. |
| 2014/0257489 A1 | 9/2014 | Warren et al. |
| 2014/0275799 A1 | 9/2014 | Schuele |
| 2014/0276840 A1 | 9/2014 | Richter et al. |
| 2014/0277204 A1 | 9/2014 | Sandhu |
| 2014/0318582 A1 | 10/2014 | Mowlai-Ashtiani |
| 2014/0357945 A1 | 12/2014 | Duckworth |
| 2015/0018623 A1 | 1/2015 | Friedrich et al. |
| 2015/0065795 A1 | 3/2015 | Titus |
| 2015/0073218 A1 | 3/2015 | Ito |
| 2015/0112398 A1 | 4/2015 | Morgenstern Lopez et al. |
| 2015/0164496 A1 | 6/2015 | Karpowicz et al. |
| 2015/0216593 A1 | 8/2015 | Biyani |
| 2015/0223676 A1 | 8/2015 | Bayer et al. |
| 2015/0230697 A1 | 8/2015 | Phee et al. |
| 2015/0342621 A1 | 12/2015 | Jackson, III |
| 2015/0374213 A1 | 12/2015 | Maurice, Jr. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0213500 A1 | 7/2016 | Beger et al. |
| 2016/0228280 A1 | 8/2016 | Schuele et al. |

(56) References Cited

U.S. PATENT DOCUMENTS

| | | |
|---|---|---|
| 2016/0235284 A1 | 8/2016 | Yoshida et al. |
| 2016/0287264 A1 | 10/2016 | Chegini et al. |
| 2016/0296220 A1 | 10/2016 | Mast et al. |
| 2016/0353978 A1 | 12/2016 | Miller et al. |
| 2017/0003493 A1 | 1/2017 | Zhao |
| 2017/0007226 A1 | 1/2017 | Fehling |
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0086939 A1 | 3/2017 | Vayser et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |
| 2017/0360291 A1 | 12/2017 | Chegini et al. |
| 2019/0209002 A1 | 7/2019 | Chegini et al. |

FOREIGN PATENT DOCUMENTS

| | | |
|---|---|---|
| DE | 29916026 U1 | 11/1999 |
| EP | 0 537 116 A1 | 4/1993 |
| EP | 0 807 415 A2 | 11/1997 |
| EP | 2422722 A1 | 2/2012 |
| GB | 2481727 A | 1/2012 |
| GB | 2489492 A | 10/2012 |
| JP | 2008-017903 A | 1/2008 |
| JP | 2008-229167 A | 10/2008 |
| WO | 96/29014 A1 | 9/1996 |
| WO | 2001/056490 A1 | 8/2001 |
| WO | 2001/089371 A1 | 11/2001 |
| WO | 2002/002016 A1 | 1/2002 |
| WO | 2004021898 A1 | 3/2004 |
| WO | 2004/103430 A2 | 12/2004 |
| WO | 2008/121162 A1 | 10/2008 |
| WO | 2009/033207 A1 | 3/2009 |
| WO | 2010/059383 A2 | 5/2010 |
| WO | 2013/033426 A2 | 3/2013 |
| WO | 2013/059640 A1 | 4/2013 |
| WO | 2014/050236 A1 | 4/2014 |
| WO | 2014/100761 A2 | 6/2014 |
| WO | 2014/185334 A1 | 11/2014 |
| WO | 2016/111373 A1 | 7/2016 |
| WO | 2016/131077 A1 | 8/2016 |
| WO | 2016/168673 A1 | 10/2016 |
| WO | 2017/006684 A1 | 1/2017 |
| WO | 2017/015480 A1 | 1/2017 |
| WO | 2017/083648 A1 | 5/2017 |

OTHER PUBLICATIONS

U.S. Appl. No. 14/546,620, filed Nov. 18, 2017, Proximal-End Securement of a Minimally Invasive Working Channel.
U.S. Appl. No. 15/695,046, filed Sep. 5, 2017, Proximal-End Securement of a Minimally Invasive Working Channel.
U.S. Appl. No. 16/358,372, filed Mar. 19, 2019, Proximal-End Securement of a Minimally Invasive Working Channel.
**International Search Report and Written Opinion for Application No. PCT/US2015/043554, dated Nov. 19, 2015 (8 pages).
**International Search Report and Written Opinion for Application No. PCT/US2015/048485, dated Feb. 9, 2016 (16 pages).
**International Search Report and Written Opinion for Application No. PCT/US2015/060978, dated Feb. 15, 2016 (8 pages).
**Invitation to Pay Additional Fees for Application No. PCT/US2016/050022, dated Nov. 3, 2016 (2 pages).
**International Search Report and Written Opinion for Application No. PCT/US2016/050022, dated Feb. 1, 2017 (19 pages).
International Search Report for Application No. PCT/US2018/047133, dated Dec. 20, 2018 (6 Pages).
**Iprenburg, M, "Percutaneous Transforaminal Endoscopic Discectomy: The Thessys Method," in Lewandrowski, K., et al, Minimally Invasive Spinal Fusion Techniques, Summit Communications, 2008 pp. 65-81.
Japanese Office Action for Application No. 2017-544858, dated May 28, 2019 (5 pages).
*Jung, K., et al., "A hands-free region-of-interest selection interface for solo surgery with a wide-angle endoscope: preclinical proof of concept," Surg Endosc, 2017, v. 31, pp. 974-980.
European Office Action dated Nov. 27, 2019 for Application No. 15766321.2 (10 pages).

* cited by examiner

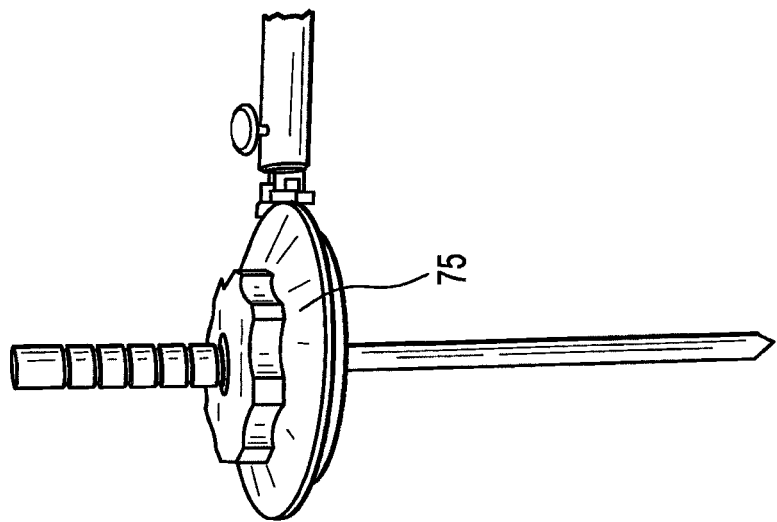
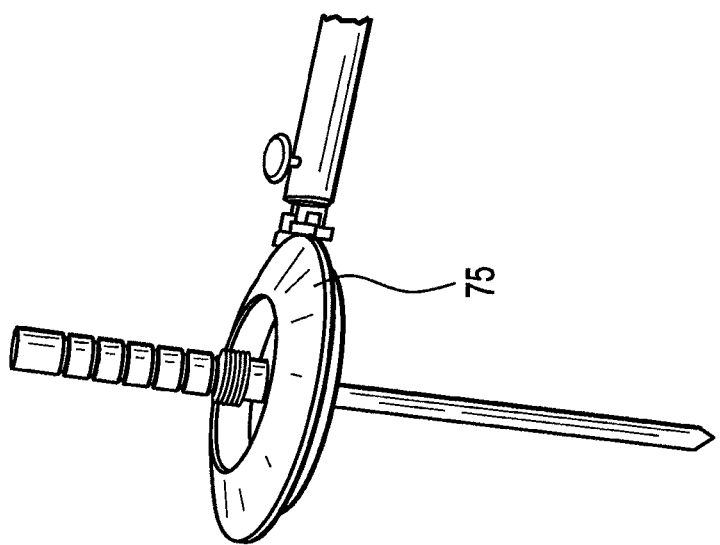
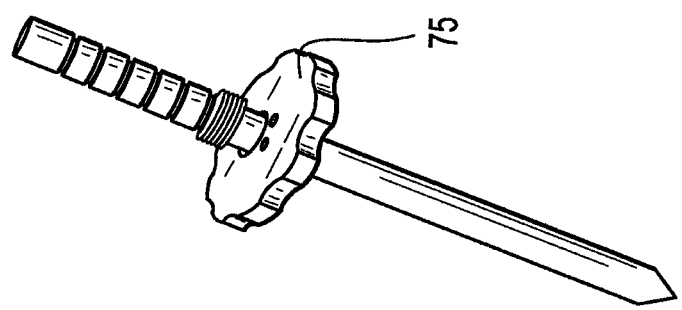

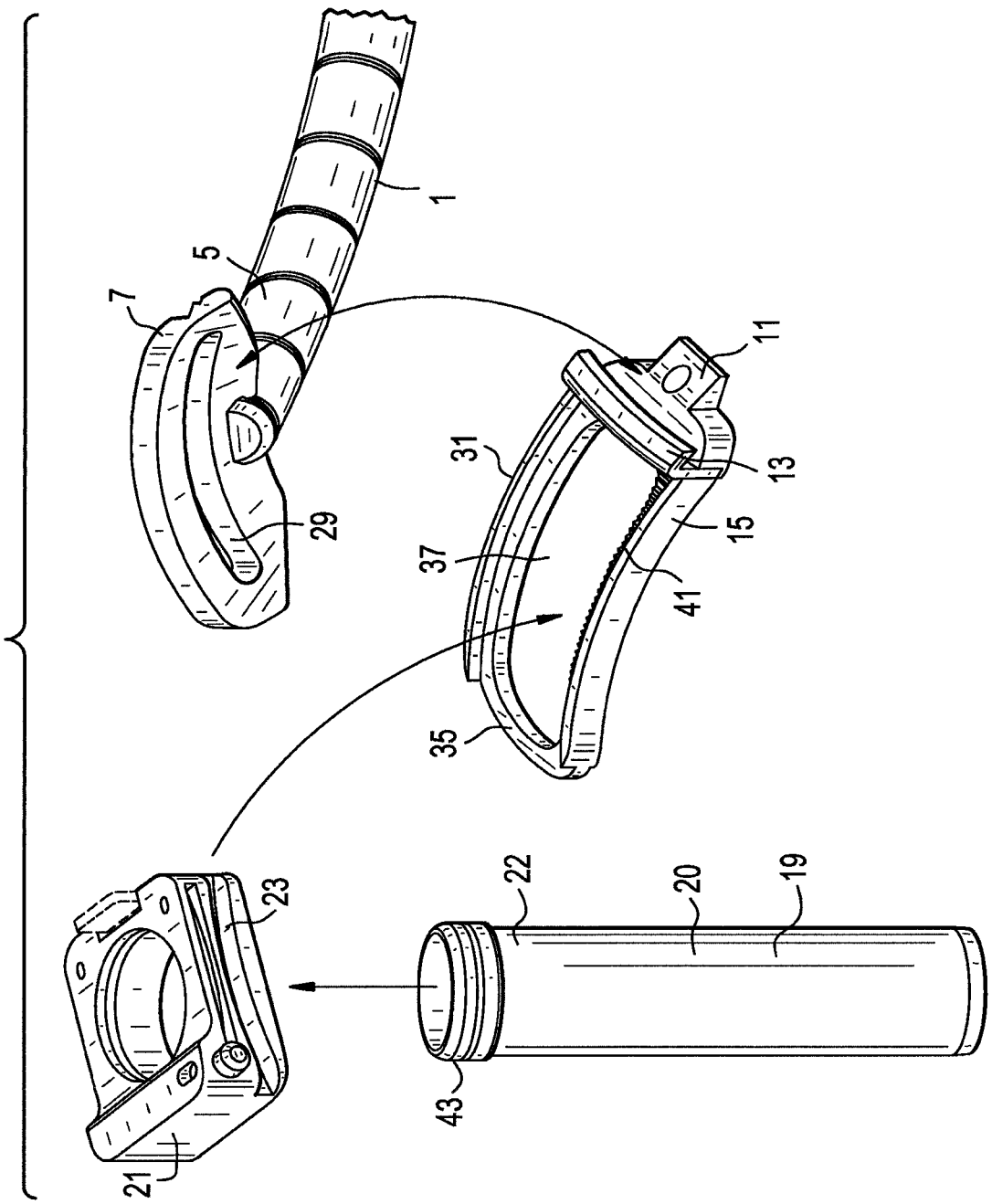

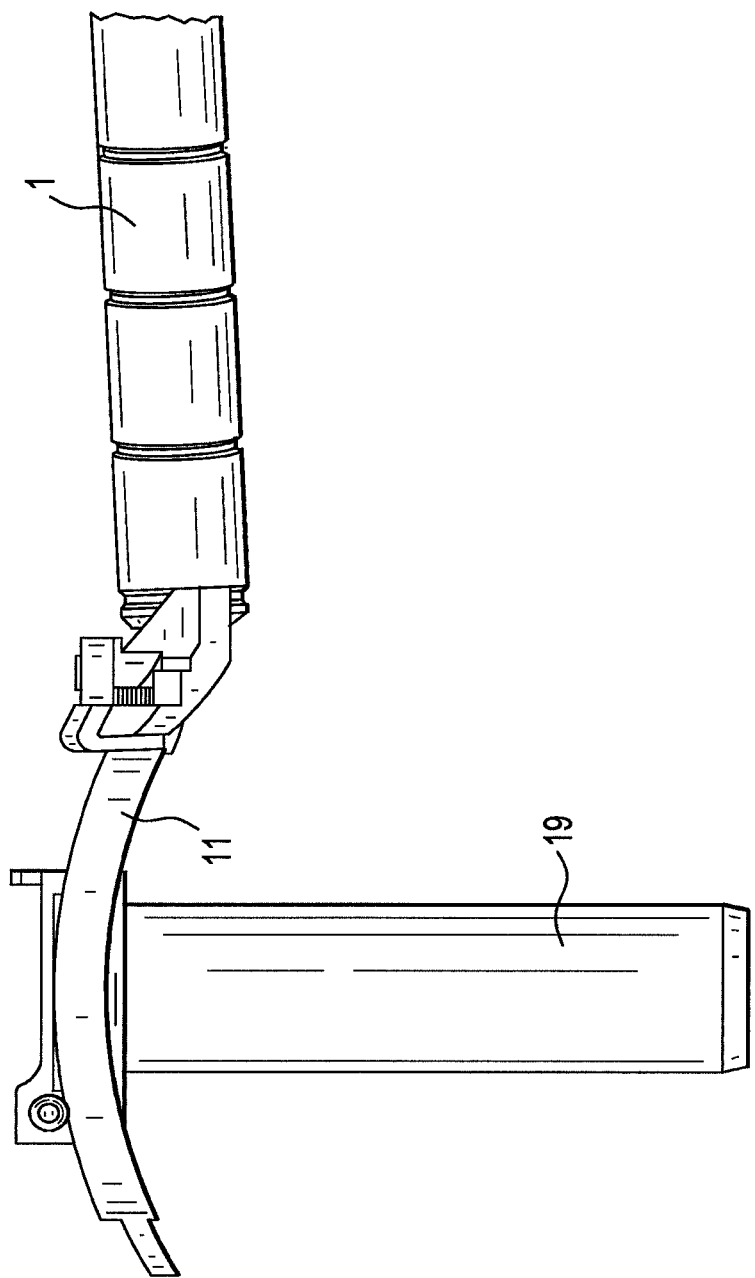

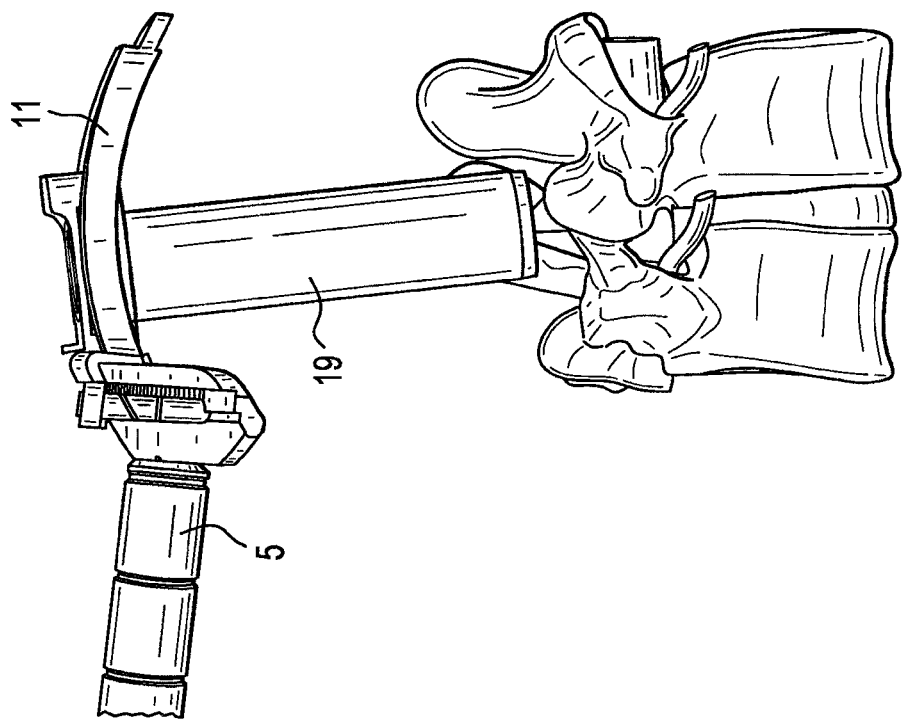
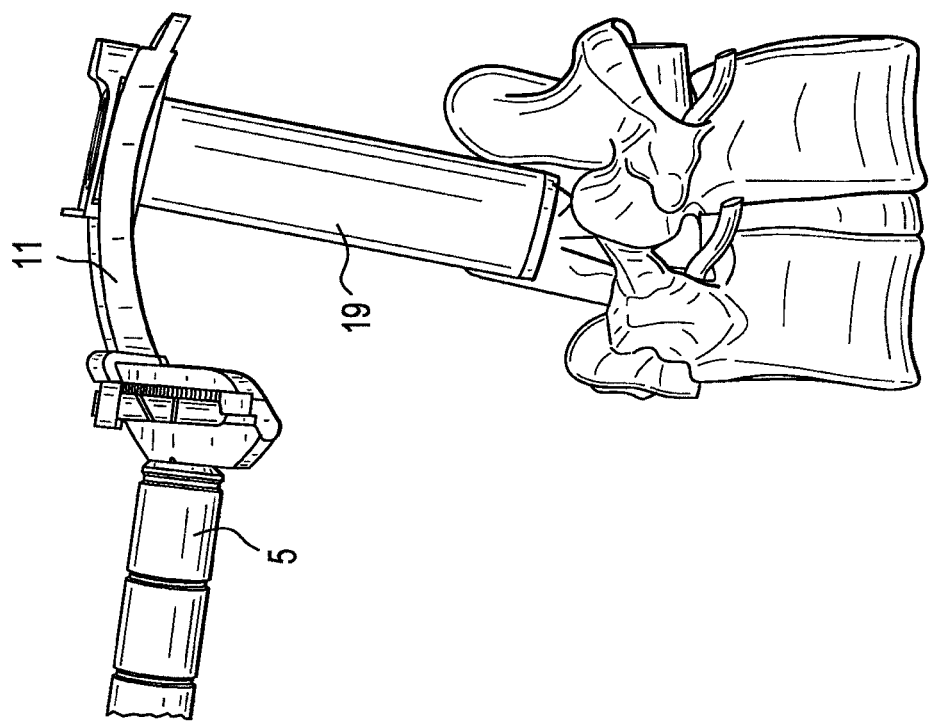

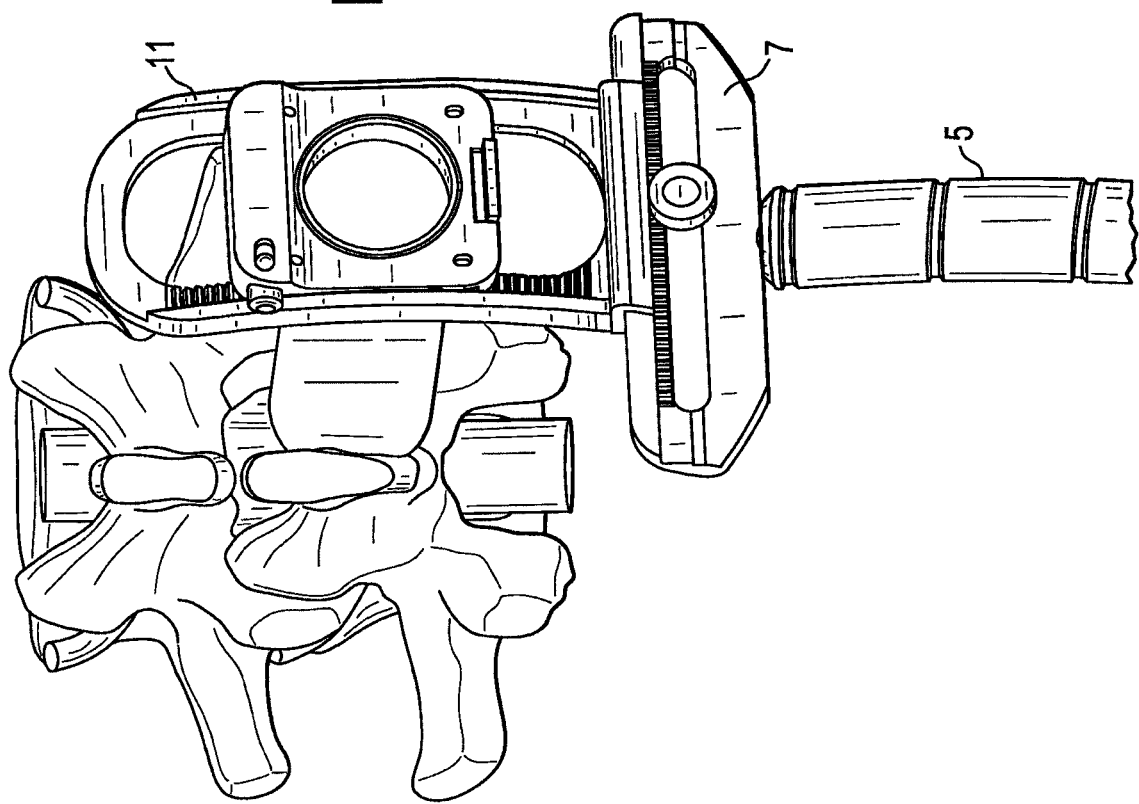

PROXIMAL-END SECUREMENT OF A MINIMALLY INVASIVE WORKING CHANNEL

CONTINUING DATA

This application is a continuation of U.S. patent application Ser. No. 14/546,620, filed on Nov. 18, 2014, which is a continuation-in-part of U.S. patent application Ser. No. 14/481,822, entitled "Proximal-End Securement of a Minimally Invasive Working Channel", filed on Sep. 9, 2014, Chegini et al., now issued as U.S. Pat. No. 9,924,979, on Mar. 27, 2018, each of which are incorporated by reference in their entirety.

BACKGROUND OF THE INVENTION

The general trend in the treatment of the spinal pathologies is toward minimally invasive approaches to reduce the trauma on the surrounding tissues during the operation. For treatment of the lumbar spine pathologies, a percutaneous approach may be chosen within a working channel of 4-12 mm. The working channel serves as a safety barrier between the working instruments and the sensitive tissues (e.g. nerves and blood vessels) during the operation. The process of treatment including disc removal, endplate preparation, implant insertion and graft material insertion should be performed through the working channel.

SUMMARY OF THE INVENTION

In order to ensure the safety of these procedures, the distal end portion of the working channel (from surgeon's perspective) should be secured/anchored onto desired points (see FIGS. 1A and 1B). Typically, these points are either bone or disc tissue. In addition to the fixation of the distal end portion of the working channel, depending on the procedure that is being performed, the proximal end portion of the working channel needs to be able to either move laterally, move cranially/caudally, or be substantially fixed. For example, during disc removal, the surgeon might want to change the angle of the working channel in order to gain better access to more of the remaining disc tissue (see FIG. 1B). At the same time, it might be desired that this motion be limited to a given range, and to be fixed in the axial direction. Furthermore, in some instances, it might be desired for the proximal portion of the working channel to be fully fixed in order to create a two-point fixed channel between proximal and distal portion.

Therefore, the present invention is directed at minimally invasive systems in which the proximal end portion of the working channel has either zero or a limited range of movement in the lateral direction.

Therefore, in accordance with the present invention, there is provided a minimally-invasive surgical access system, comprising;
 a) a tube having an outer wall, a longitudinal bore, a proximal end portion and a distal end portion;
 b) a sliding tab comprising a collar having a pair of opposed flanges extending therefrom, wherein the collar is slidable along the outer wall of the tube; and
 c) an annular frame having a pair of substantially opposed slots,
wherein the flanges of the collar respectively extend through the slots of the annular frame, and
wherein the tube extends through the annular frame.

Therefore, in accordance with the present invention, there is provided a minimally-invasive surgical access system, comprising;
 a) a tube having an outer wall, a longitudinal bore, a proximal end portion, a distal end portion, and a substantially spherical element radially surrounding a segment of the outer wall;
 b) a sliding tab having a base and a pair of opposed flanges extending therefrom; the base having a hole therethrough defining a rim having a static portion and a slidable portion,
 c) an annular frame having a pair of substantially opposed slots,
wherein each flange of the sliding tab extends through a respective slot of the annular frame,
wherein the tube extends through the annular frame, and
wherein the static portion of the rim releasably contacts a first portion of the substantially spherical element and the slidable portion of the rim releasably contacts a second portion of the substantially spherical element.

Therefore, in accordance with the present invention, there is provided a minimally invasive surgical access system, comprising;
 a) an upper cap describing a first portion of a substantially spherical surface,
 b) an middle cap describing a second portion of the substantially spherical surface and having a central hole,
 c) a lower cap describing a third portion of the substantially spherical surface,
 d) a tube having an outer wall having an attachment portion, a longitudinal bore, a proximal end portion, a distal end portion,
wherein the upper cap and the lower cap are attached to and radially extend from the outer wall of the tube,
wherein at least one of the upper cap and the lower cap is removably attached to the outer wall of the tube,
wherein the tube is received in the central hole of the middle cap, and
wherein the middle cap is received between the upper cap and the lower cap.

DESCRIPTION OF THE FIGURES

FIGS. 5A-C disclose the different steps of mounting and securing the embodiment of FIG. 4.
FIG. 6A discloses an exploded view of the apparatus of the fourth embodiment of the present invention.
FIGS. 6C, 6K, 6L, 6M, 6N and 6O disclose various desirable orientations of the fourth apparatus embodiment relative to a functional spinal unit.

FIGS. 6H-6J disclose respective side, perspective and top views of the fourth embodiment apparatus.

FIGS. 6K-6O disclose various views of the apparatus in relation to the spine.

FIGS. 6P-6Q disclose views of the fourth embodiment apparatus wherein the medial-lateral bar runs parallel to the spine.

DETAILED DESCRIPTION OF THE INVENTION

For the purposes of the present invention, the "distal end portion of the tube" is the portion of the tube that is nearest to the patient and furthest from the surgeon when the tube is inserted into the patient, and the "proximal end portion of the tube" is the portion of the tube that is furthest from the patient and nearest to the surgeon when the tube is inserted into the patient. Also, "a working channel" and "a tube" are considered to be interchangeable.

In the following description, several concepts are described covering the subjects of a) limiting lateral motion of the proximal end portion of the tube, b) eliminating the lateral motion of the proximal end portion of the tube, and c) eliminating the axial motion of the proximal end portion of the tube.

Figure 1A:
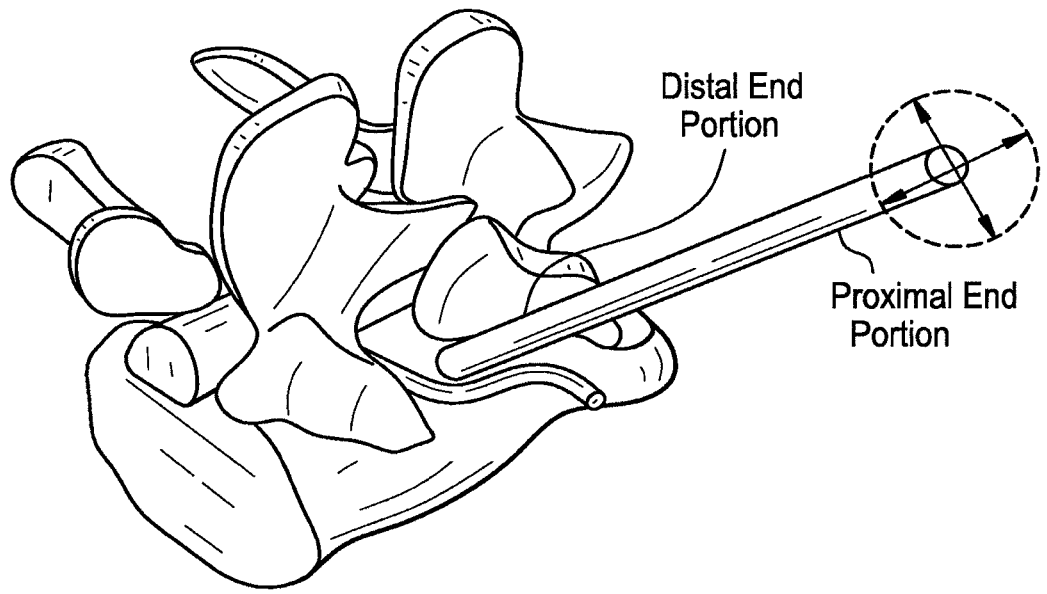
FIGS. 1A and 1B disclose the desired ranges of motion for the systems of the present invention.
Figure 1B:
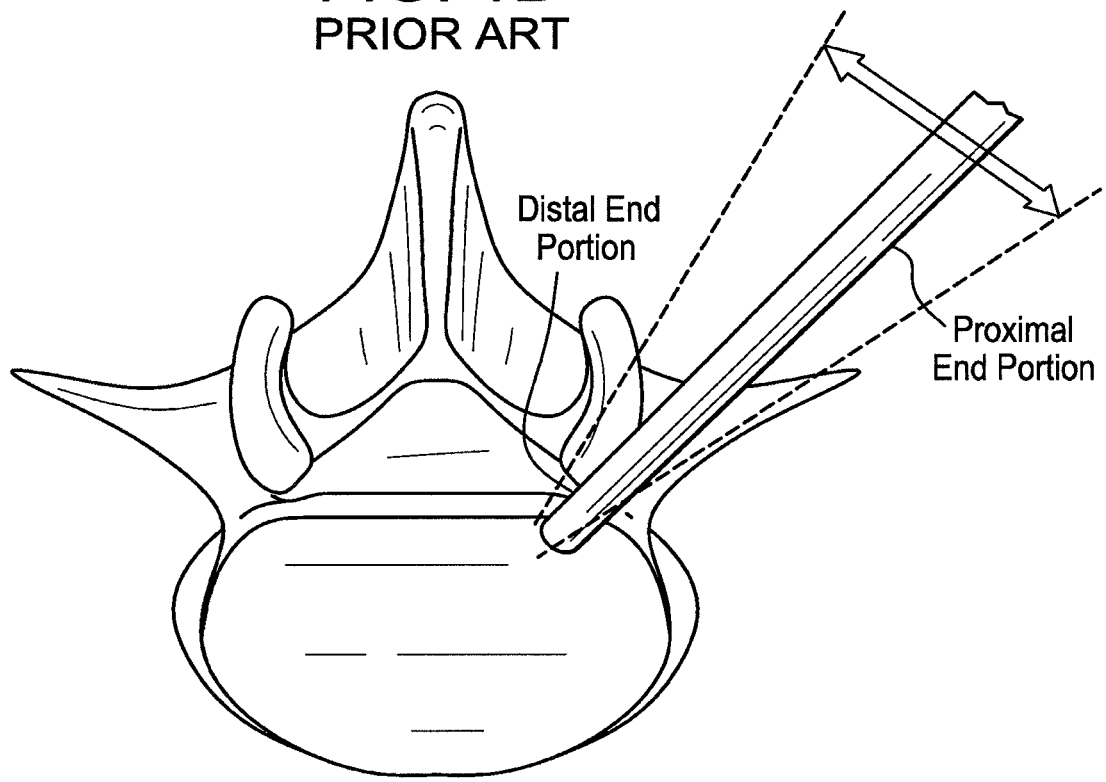
Figure 2:
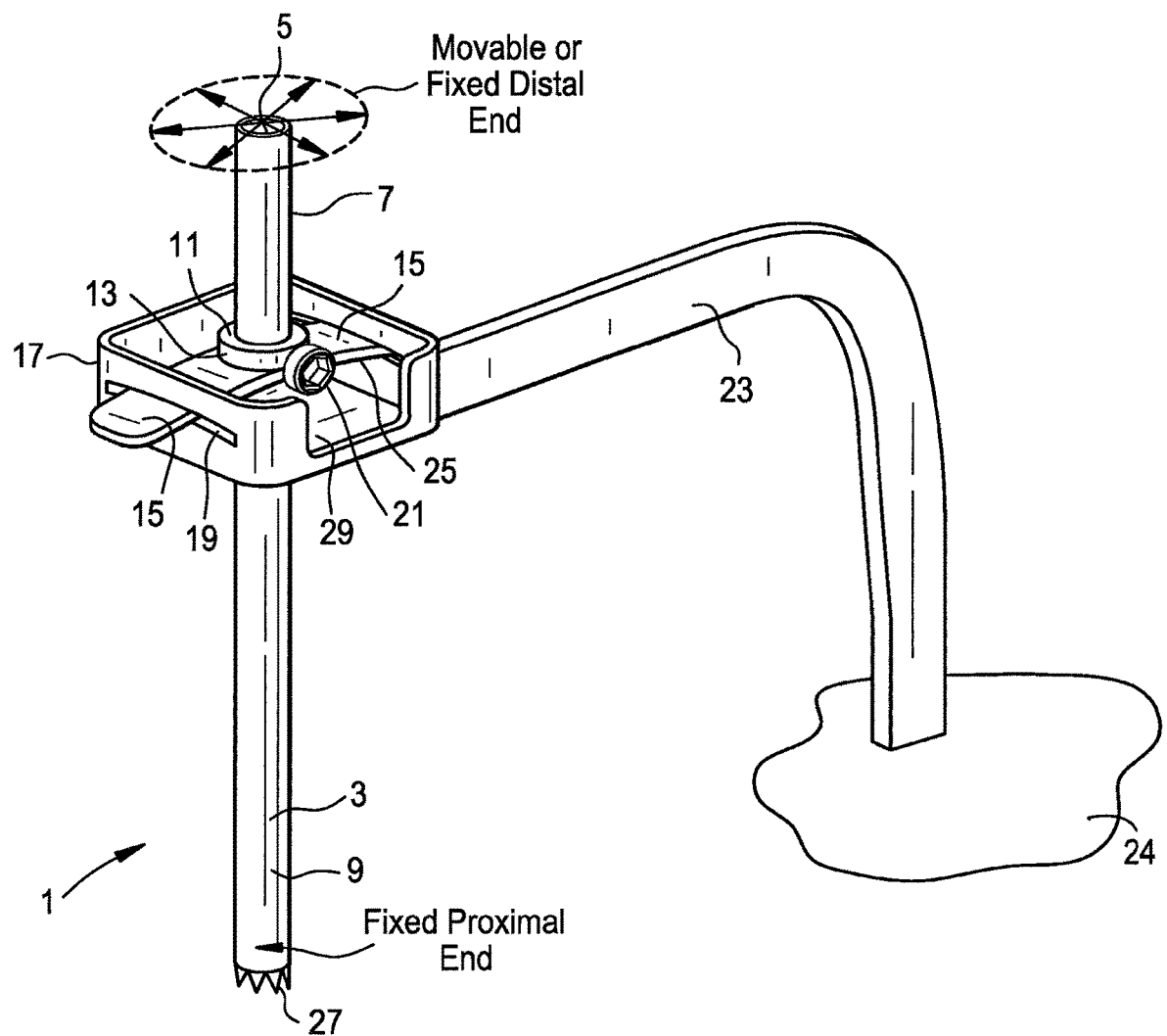
FIG. 2 discloses a first embodiment of the present invention having a slidable collar.

Now referring to FIG. 2, there is provided a minimally—invasive surgical access system, comprising;
a) a tube 1 having an outer wall 3, a longitudinal bore 5, a proximal end portion 7 and a distal end portion 9;
b) a sliding tab 11 comprising a collar 13 having a pair of opposed flanges 15 extending therefrom, wherein the collar is slidable along the outer wall of the tube; and
c) an annular frame 17 having a pair of substantially opposed slots 19,
wherein the flanges of the collar respectively extend through the slots of the annular frame, and
wherein the tube extends through the annular frame.

The embodiment shown in FIG. 2 includes an annular frame that can be fixed onto a stationary unit, such as the operating table, so as to anchor the system. As previously described, the distal end portion of the tube can be fixed onto the bony structures (such as a vertebral body) or soft tissues (such as disc cartilage) within the lumbar spine. When the tube is so distally anchored, the proximal end portion of the tube can move in a substantially conical volume, with the distal end of the tube being its apex. The fixed-in-space annular frame of the embodiment of FIG. 2 limits the range of the motion of the proximal end portion of the tube. The sliding tab component of the system is comprised of a collar with a pair of opposed flanges extending therefrom. Preferably, the shape of the flanges describes a portion of a spherical surface that mimics the limited motion of the tube. The outer annular frame has a pair of opposed matching slots that slidably receive their respective flanges. Preferably, each slot is shaped as an arc that matches the arc-like transverse cross-section of the flange it receives. The working channel is mounted and fixed onto the sliding tab using a set screw 21 that is received in a threaded hole in the collar. The set screw can extend through the collar and contact the outer wall of the tube in the proximal end portion of the tube so as to lock the collar to the tube, thereby preventing the motion of the tube channel in the axial direction. The limits of the lateral motion of the proximal end portion are defined by the outer annular frame. The outer annular frame can be fixed onto the operating table 24 using an extension arm 23.

Therefore, in preferred embodiments of the first embodiment of the present invention, the system further comprises an arm extending from a stationary unit, wherein the arm is attached to the annular frame. Preferably, the collar comprises a threaded hole, and the system further comprises a set screw received in the threaded hole of the collar. Preferably, the set screw can extend through the collar and contact the outer wall of the tube in the proximal end portion of the tube to lock the collar to the tube. Preferably, each flange comprises a portion of a spherical surface 25 and each slot describes an arc, wherein the flange mates with the slot. Preferably, the distal end portion of the tube has a docking feature (such as a plurality of distally-extending teeth 27) adapted to dock to bone or cartilage. In some embodiments, the collar does not contact the annular frame. In some embodiments, the annular frame has a cutout 29 adapted to allow access by a screwdriver to the collar in order to tighten or loosen the set screw. Preferably, this cutout aligns radially with the set screw. Preferably, the proximal end portion of the tube is able to move in a substantially frustoconical volume when the distal end portion of the tube is fixed.

Figure 3:
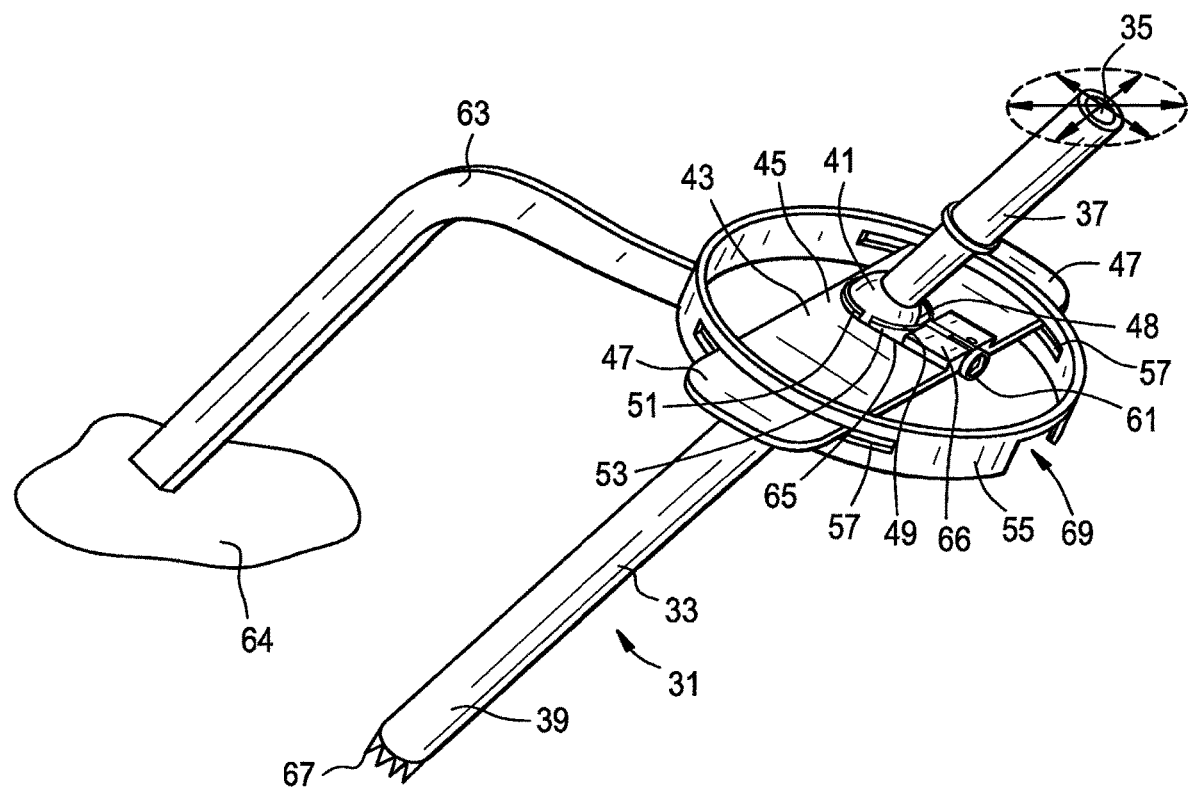
FIG. 3 discloses a second embodiment of the present invention having a substantially sphereical element attached to the tube.

Now referring to FIG. 3, there is provided a minimally-invasive surgical access system, comprising;
a) a tube 31 having an outer wall 33, a longitudinal bore 35, a proximal end portion 37, a distal end portion 39, and a substantially spherical element 41 radially surrounding a segment of the outer wall;
b) a sliding tab 43 having a base 45 and a pair of opposed flanges 47 extending therefrom; the base having a hole 48 therethrough defining a rim 49 having a static portion 51 and a slidable portion 53,
c) an annular frame 55 having a pair of substantially opposed slots 57,
wherein each flange of the sliding tab extends through a respective slot of the annular frame,
wherein the tube extends through the annular frame, and
wherein the static portion of the rim releasably contacts a first portion of the substantially spherical element and the slidable portion of the rim releasably contacts a second portion of the substantially spherical element.

The second embodiment of FIG. 3 includes an outer annular frame that could be fixed onto a stationary unit, such as the operating table. As previously described, the distal end portion of the tube can be fixed onto the bony structures or soft tissues of the spine, so that the proximal end portion of the tube can move in a substantially frustoconical volume with the distal tip being the apex. In this particular embodiment, the sliding tab has flat flanges, which are easier to manufacture. Likewise, the outer annular frame has a pair of simple, linear slots to slidably receive the flanges. The sliding tab has an axial hole therein defining a rim, the rim comprising a static hemispherical portion, as well as a movable hemispherical portion. As the working channel passes into the sliding-tab, the set screw 61 can be turned to move the dynamic hemisphere to hold or release the spherical protrusion of the working channel, thereby fixing or release the angel of the sliding tab with respect to the tube. This allows for the movement on the desired range. The whole structure allows for sideways motion of the distal end in a given range (defined by the slot on the outer frame) and blocks the axial motion of the distal end.

Preferably, in this second embodiment, the system further comprises an arm 63 extending from a stationary unit 64, wherein the arm is attached to the annular frame. Preferably, the base comprises a first cutout 65, and further comprises a sliding door 66 slidably received in the cutout. Preferably, the sliding door comprises the second portion of the rim. Preferably, the sliding door further comprises a substantially hemispherical portion extending from the slidable portion of the rim, wherein the substantially hemispherical portion releasably contacts the second portion of the substantially spherical element to lock the sliding tab to the tube. Preferably, the sliding door is slidably actuated by a set screw. Preferably, each flange of the sliding tab is flat and each respective slot is substantially rectangular, so that the flange mates with the slot. Preferably, the distal end portion of the tube has a docking feature (such as distally extending teeth 67) adapted to dock to bone or cartilage. In some embodiments, the substantially spherical element does not contact the annular frame. Preferably, the annular frame has a second cutout 69 (designed to allow access by a screwdriver) that aligns radially with the set screw. Preferably, the proximal end portion of the tube is able to move in a substantially frustoconical volume when the distal end portion of the tube is fixed. In some embodiments, the flat flanges of the sliding tab are not orthogonal to the tube.

Figure 4A:
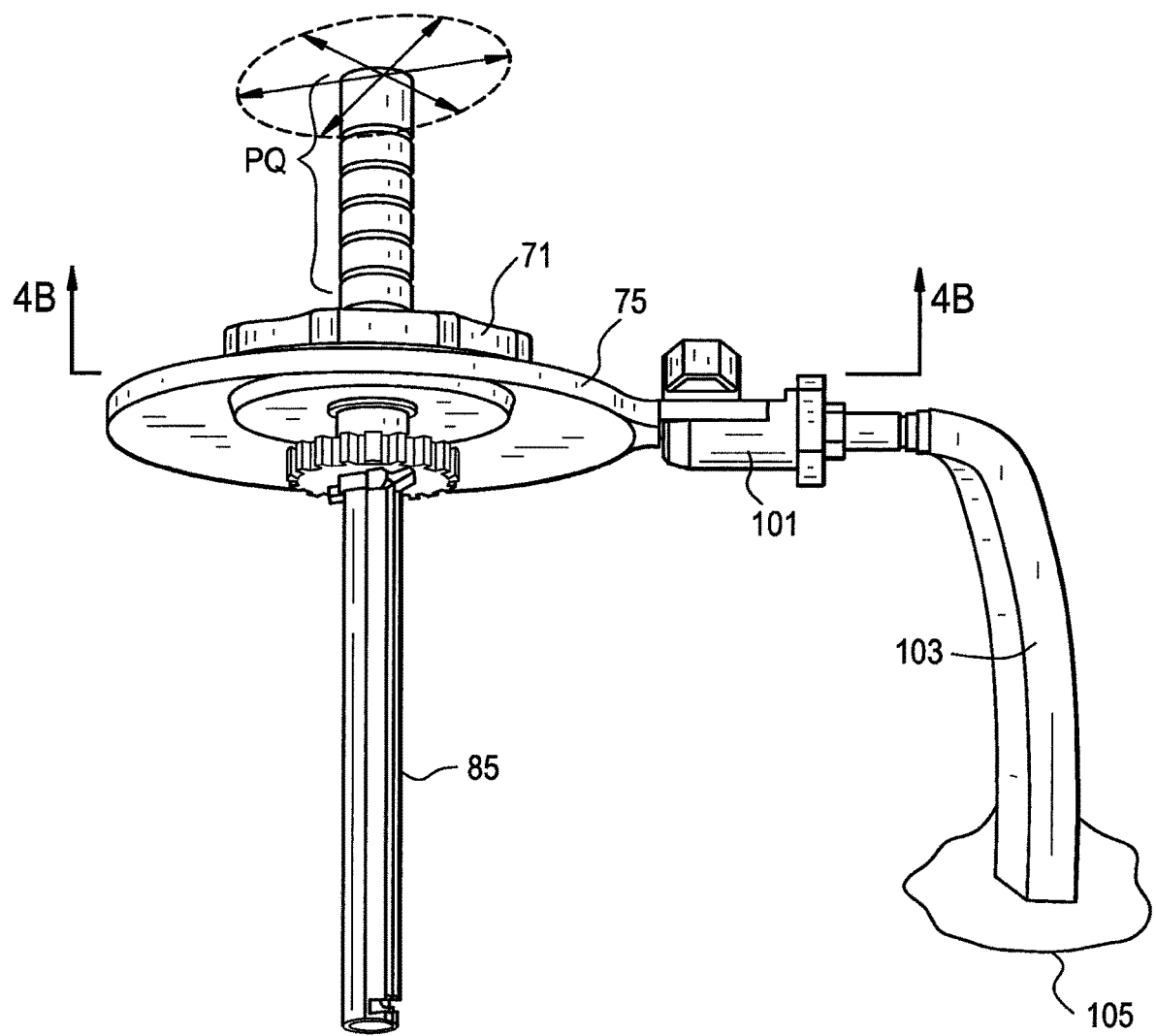
FIGS. 4A-B discloses a third embodiment of the present invention having a plurality of caps.
Figure 4B:
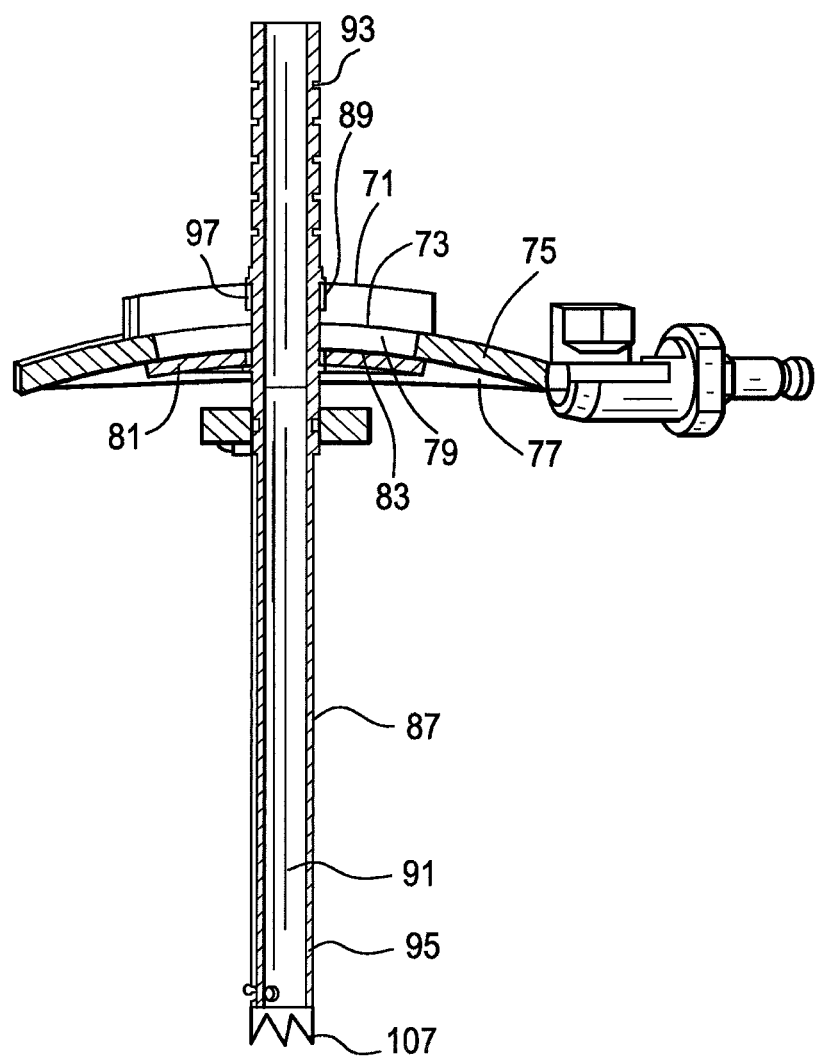

Now referring to FIGS. 4A-4B, there is provided a minimally invasive surgical access system, comprising;
- a) an upper cap 71 describing a first portion 73 of a substantially spherical surface,
- b) an middle cap 75 describing a second portion 77 of the substantially spherical surface and having a central hole 79,
- c) a lower cap 81 describing a third portion 83 of the substantially spherical surface,
- d) a tube 85 having an outer wall 87 having an attachment portion 89, a longitudinal bore 91, a proximal end portion 93, a distal end portion 95, wherein the upper cap and the lower cap are attached to and radially extend from the outer wall of the tube,
wherein at least one of the upper cap and the lower cap is removably attached to the outer wall of the tube,
wherein the tube is received in the central hole of the middle cap, and
wherein the middle cap is received between the upper cap and the lower cap.

This concept comprises three spherical caps on top of each other. The middle cap is the proximal point where the rigid arm is fixed. The lower cap extends from the working channel and is preferably integral with the working channel. This lower cap helps to prevent the working channel from being pulled proximally through the hole of the middle cap. The middle cap has a hole of predetermined size that allows for limited lateral motion of the working channel, thereby defining the boundaries of allowed motion. The middle cap is fixed to the operating table via attachments as described above. This middle cap may have a fixation element to help with the fixation. The upper cap has a threaded hole 97 and, when threaded onto the threaded 89 portion of the working channel, helps preventing the channel from advancing distally. In this concept, if the upper cap is advanced distally, it will create friction between the caps and will prevent the motion of the caps relative to each other. In other words, this concept allows for the motion of the working channel and at the same time allows for complete fixation of the distal and proximal ends of the working channel at desired direction.

Preferably, in the embodiment of FIG. 4, the upper cap is located proximal to the lower cap. Preferably, the middle cap has a fixation element 101 for fixation to a stationary unit. Preferably, the system further comprises an arm 103 extending from a stationary unit 105, wherein the arm is attached to the fixation element. Preferably, the proximal portion of the tube is able to move in a substantially frustoconical volume when the distal end portion of the tube is fixed. Preferably, the distal end portion of the tube has a docking feature 107 adapted to dock to bone. Preferably, the upper cap, middle cap, and lower cap are located in a proximal-most quarter PQ of the tube.

In some embodiments, the upper cap has a threaded hole 97, the outer wall of the working channel has a threaded portion 89, and wherein the upper cap is threadably received on the threaded portion of the outer wall of the tube.

In FIG. 4, the upper cap is shown to be removable by virtue of its threadability upon the outer wall of the tube. However, removability is not restricted to threaded features. For example, in some embodiments, the tube and cap may provide a Morse taper lock. In other embodiments, the cap is made of an elastic material that snugly fits the outer wall of the tube.

In some embodiments, one of the upper cap and the lower cap is removably attached to the outer wall of the tube, and the other is integrally attached to the outer wall of the tube.

In some embodiments, one of the upper or lower cap has a threaded hole, the outer wall has a threaded portion, and the cap having the threaded hole is threadably received on the threaded portion of the outer wall of the tube.

In some embodiments, both of the upper cap and the lower cap are removably attached to the outer wall of the tube, preferably threadably attached.

A functional prototype of this method is shown in FIGS. 5A-C, with different steps of mounting and securing. In FIG. 5A, a tube having an upper threaded portion and a lower cap permanently attached thereto is provided. In FIG. 5B, the middle cap is lowered onto the lower cap. In FIG. 5C, an upper cap with a threaded hole is placed over the middle cap and threaded onto the threaded portion of the tube, thereby trapping the middle cap between the upper and lower caps. Lastly, the middle cap is affixed to a stationary unit.

In some embodiments, the features of the upper and lower caps are reversed. Therefore, in accordance with the present invention, one of the upper cap and the lower cap is removably attached to the outer wall of the tube, and the other of the caps is integrally attached to the outer wall of the tube. Alternatively, both of the upper cap and the lower cap are removably attached to the outer wall of the tube.

It is believed that the above-described embodiments are generally suitable for use in typical percutaneous spinal surgeries, in conjunction with working channel diameters of only a few millimeters. However, there are certain spinal surgeries in which use of the above embodiments could require very large and bulky constructs. These certain surgeries (which include direct decompression surgeries performed through a mini-open posterior or para-medial approach) often require:
- a) the tube of the working channel diameter to be larger-than-usual (e.g., from about 10 mm to about 30 mm in diameter), or
- b) larger cranial-caudal and medial-lateral tilt angles, so that a larger angular range of motion is realized.

Therefore, in an effort to address these situations, in a fourth embodiment, and now referring to FIGS. 6A-6O, there is provided an apparatus comprising:
- a) an arm 1 having a proximal end portion 3 connected to a stationary object and a distal end portion 5,
- b) a medial-lateral bar 7 connected to the distal end portion of the arm and having a first rail 9;
- c) a cranial-caudal bar 11 having:
  - i) a first rail 13 in slidable engagement with the first rail of the medial-lateral bar in a first direction and
  - ii) a second rail 15 extending substantially perpendicularly from the first rail of the cranial-caudal bar;

d) a working channel construct 17 comprising:
  i) a tube 19 having an outer surface 20 and a proximal end portion 22, and
  ii) a slider 21 attached to the outer surface of the tube and having a first rail 23 in slidable engagement with the second rail of the cranial-caudal bar.

This fourth embodiment functions substantially similarly to the previously-described embodiments. For example, its working channel tube has a restricted range of motion in the axial direction. Secondly, the fourth embodiment also allows for angular movement of the proximal end of the working channel construct, so as to always leave the tube's tip in the same position. See, for example, FIGS. 6D-6G.

This fourth embodiment is especially suitable in direct decompression surgeries when a) the tube of the working channel diameter needs to be from about 10 mm to about 30 mm in diameter, or b) larger cranial-caudal and medial-lateral tilt angles are needed, so that a larger angular range of motion is needed.

Figure 6B:
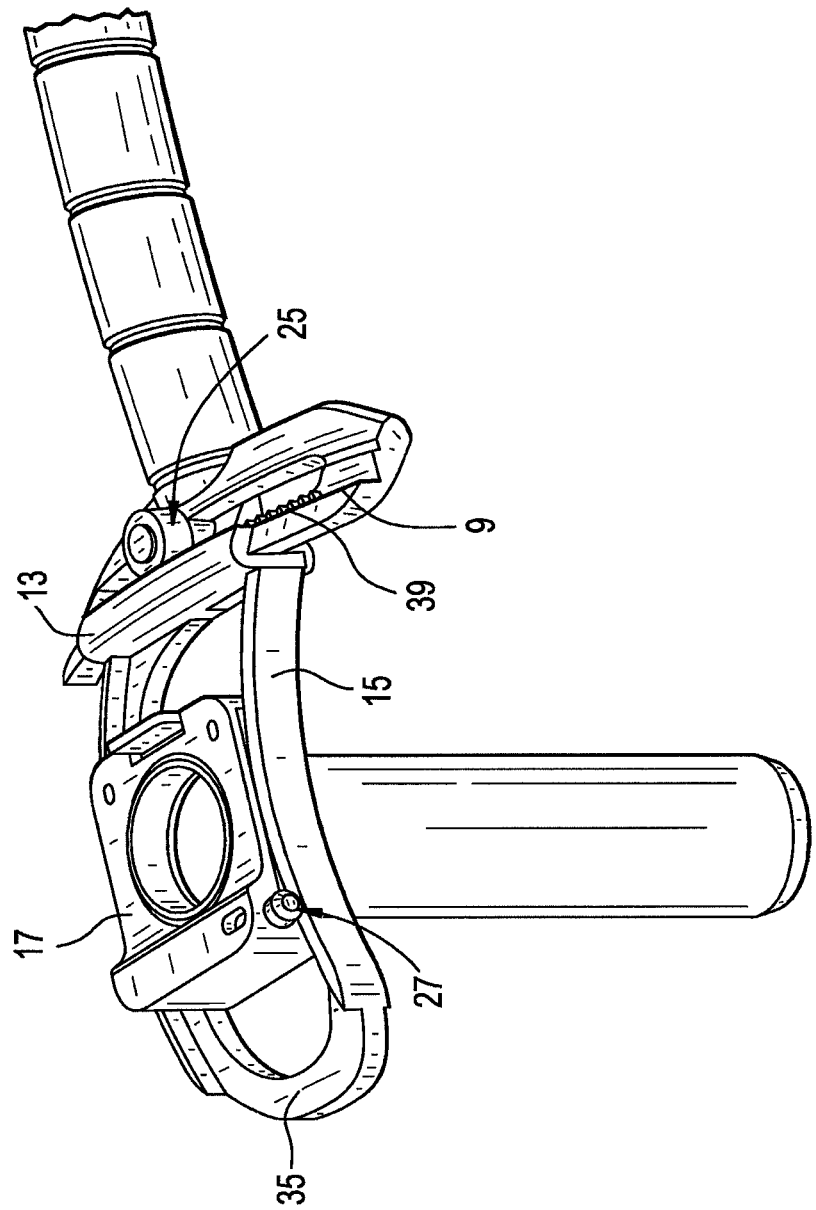
FIG. 6B discloses an assembled view of the apparatus of the fourth embodiment of the present invention.

In FIG. 6A-6B of the present invention, during the surgery, the working channel tube may be attached to and detached from a slider. Various coupling or push-button mechanisms can be selected for this attachment.

In FIGS. 6A-6O, the slider is slidably connected to the cranial-caudal bar by mating rails. Preferably, the mating rails of the slider and cranial-caudal bar have mating arcuate shapes. See FIGS. 6D-6E. Preferably, the curvature of these arcuate rails is selected so that the common radius defined by their curves corresponds to the distance between the curve location and the tip of the working channel tube in the final assembly. In other words, the distal tip of the working channel tube defines the centerpoint of the circle described by the mating rails. In this way, it is insured that when the position of the slider along the rail of the cranial-caudal bar is changed in space, the location in space of the centerpoint tube distal end does not change, only the direction of the working channel tube central axis changes. Typically, the curved slider rail can smoothly glide along its mating curved rail of the cranial-caudal bar (thereby continuously changing the cranial-caudal angle of the working channel construct). However, in some embodiments, the relative positions of these rails against each other can be fixed. Various mechanisms can be selected to fix a relative position of these rails. For example, opposing teeth can be provided along each of the mating rails, as in FIG. 6A. These teeth can act as anchors when a fixation is desired. This fixation defines the cranial-caudal angle of the working channel tube.

In FIGS. 6A-6O, the first and second rails of the cranial-caudal bar are each arcuate. Preferably, the arcs of these rails are equal, so that the cranial-caudal bar defines a spherical surface. The center of the sphere is defined by the tip location of the working channel construct in the final assembly. The rail of the medial-lateral bar mates with the first rail of the cranial-caudal bar and so also preferably has an arcuate shape of the same radius. The two bar components are slidably connected to each other by these arcuate rails. A bolt-slot connection or similar construct can be used to slidably connect the two bars in order to assure that the cranial-caudal bar not only keeps its perpendicular orientation relative to the medial-lateral bar, but is also able to slide along the slot. The position of the cranial-caudal bar relative to the medial-lateral bar defines the medial-lateral angle of the working channel construct. The position can be fixed if desired. Various mechanisms can be considered to realize the position of fixation. For example, teeth can be provided along each rail that act as anchors.

Figure 6C:
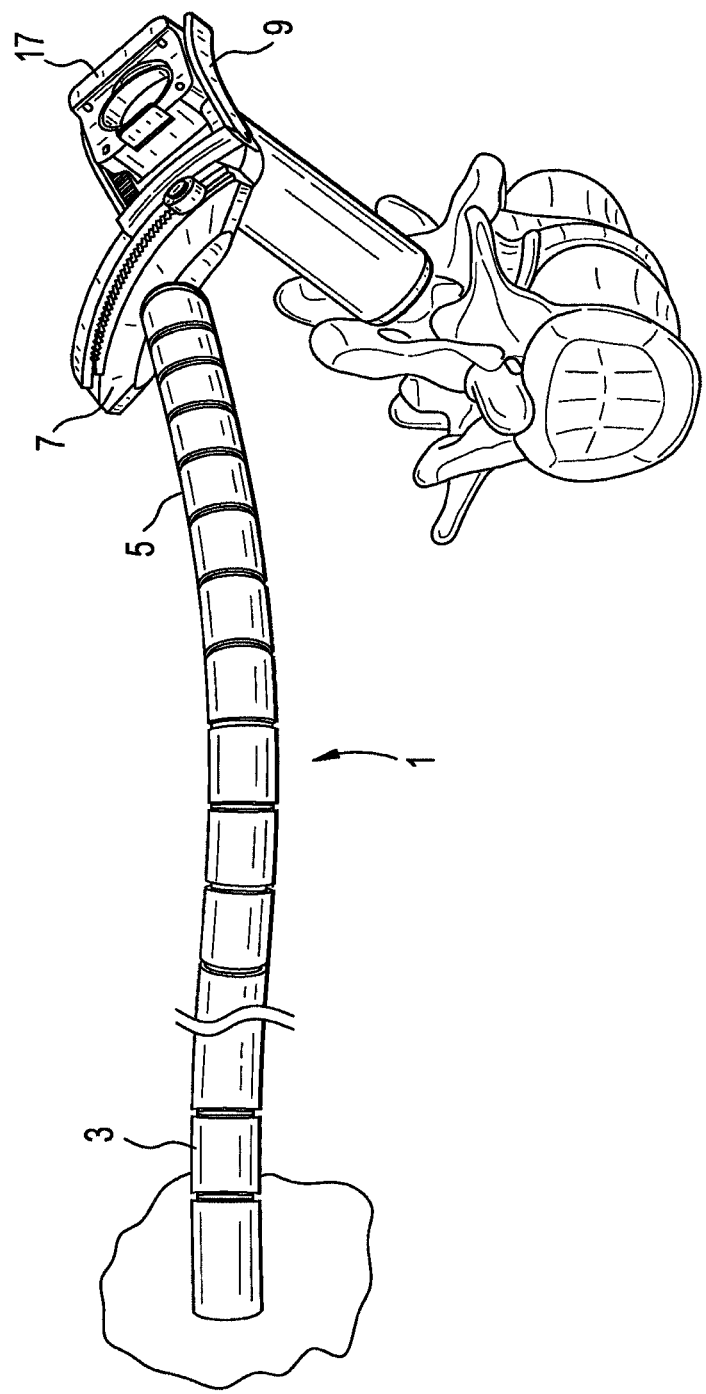
Figure 6D:
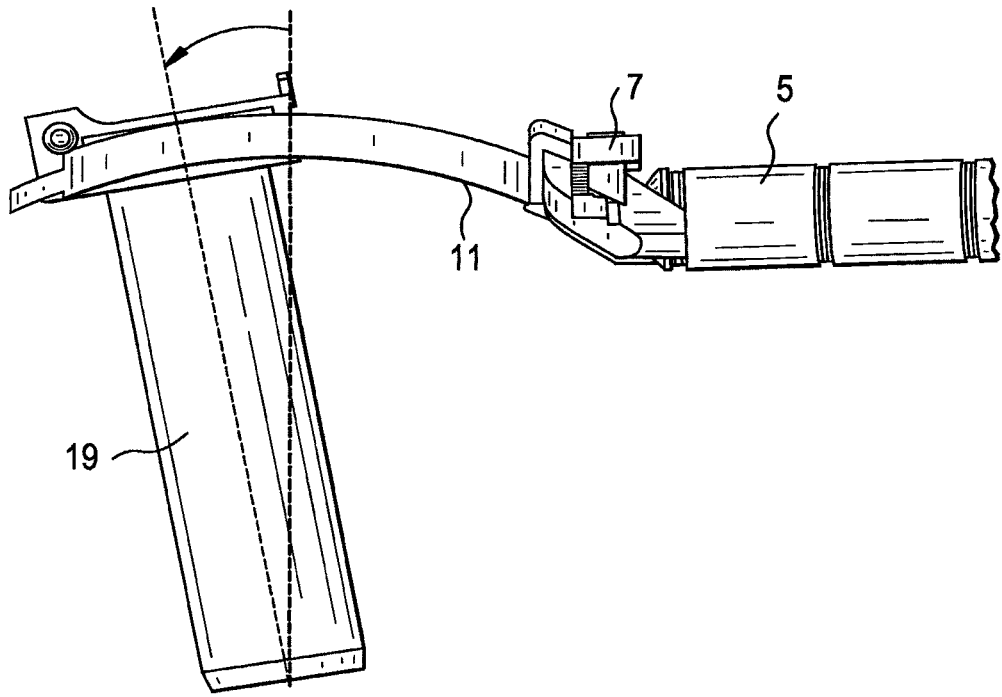
FIGS. 6D-6E disclose the possible cranial-caudal tilt angles of the fourth embodiment.
Figure 6E:
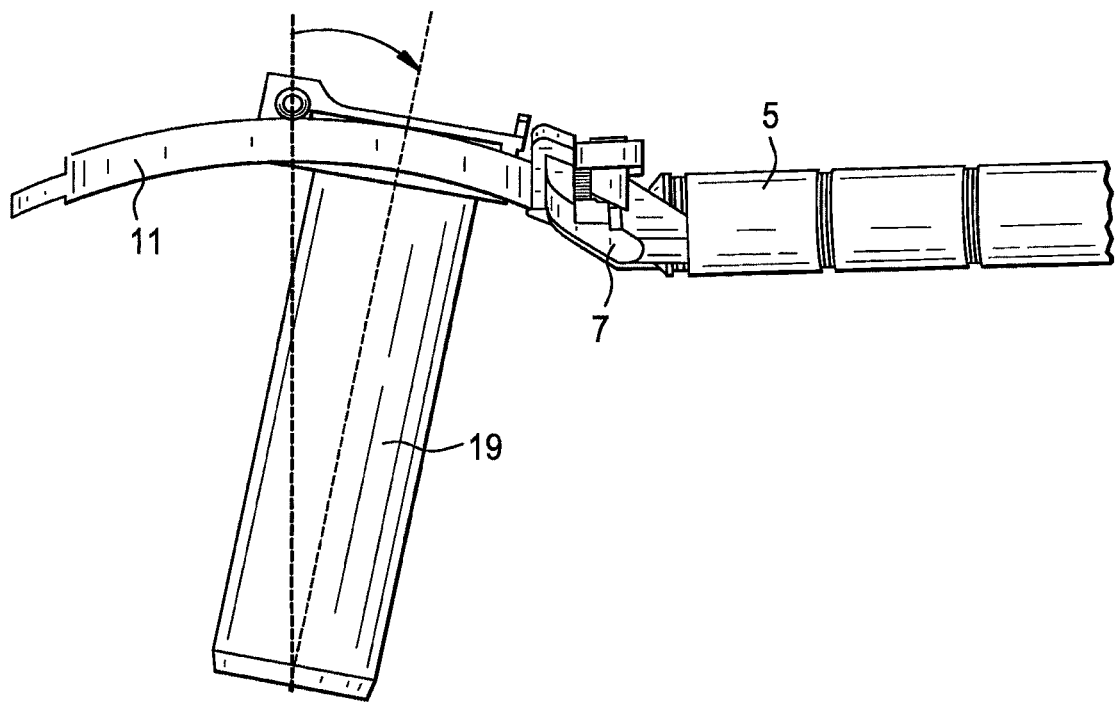
Figure 6F:
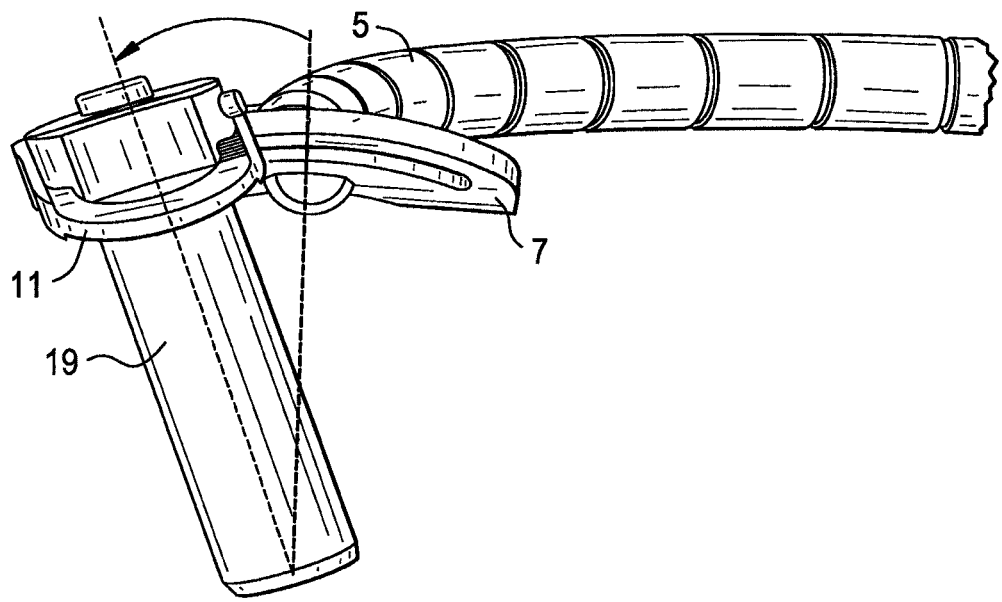
FIGS. 6F-6G disclose the possible medial-lateral tilt angles of the fourth embodiment.
Figure 6G:
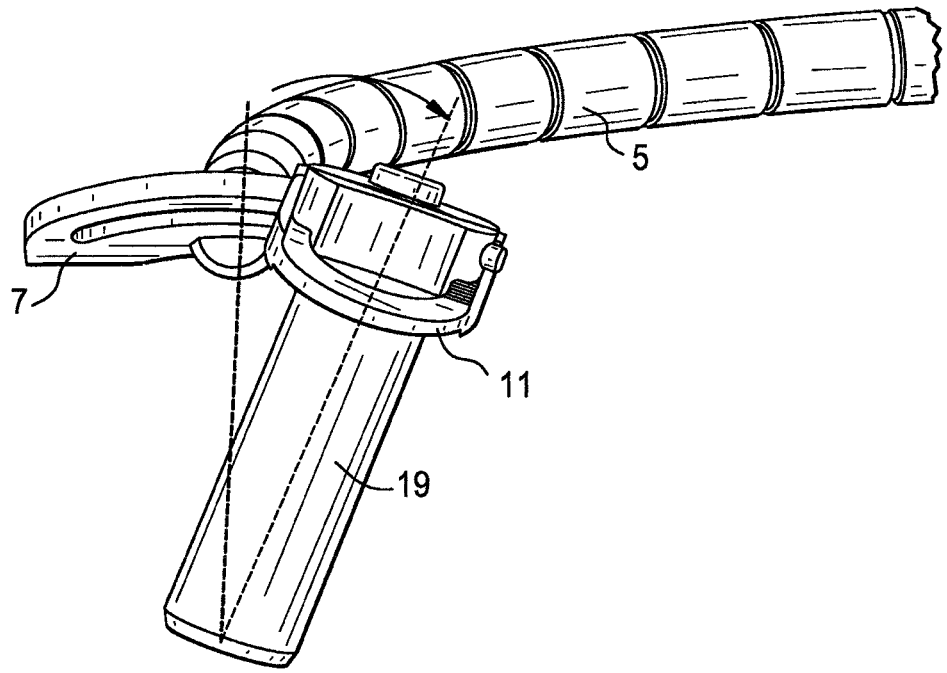
Figure 6I:
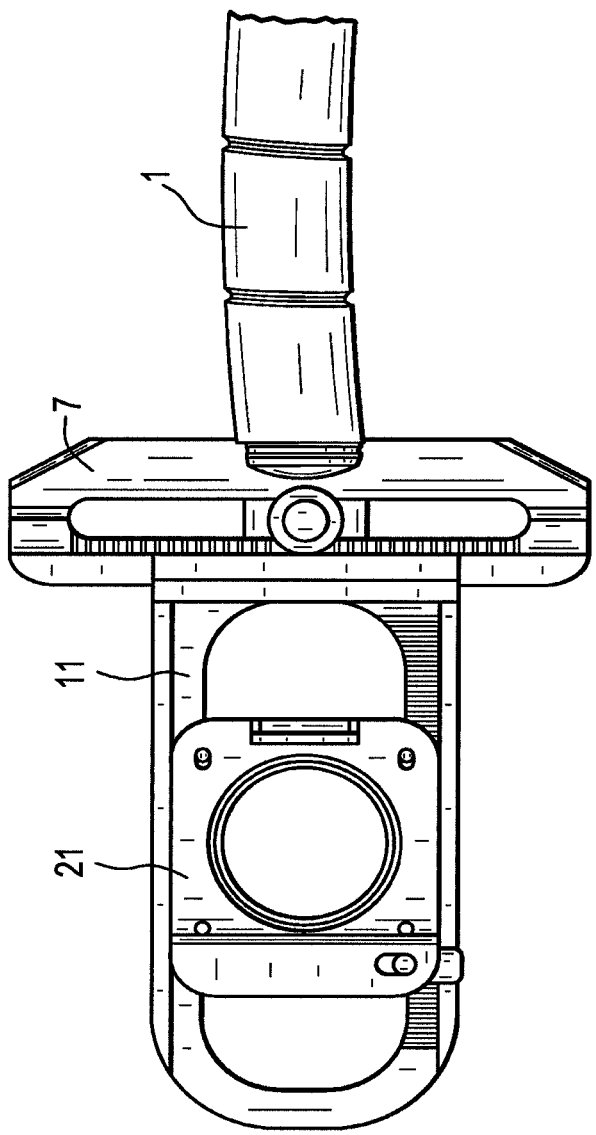
Figure 6J:
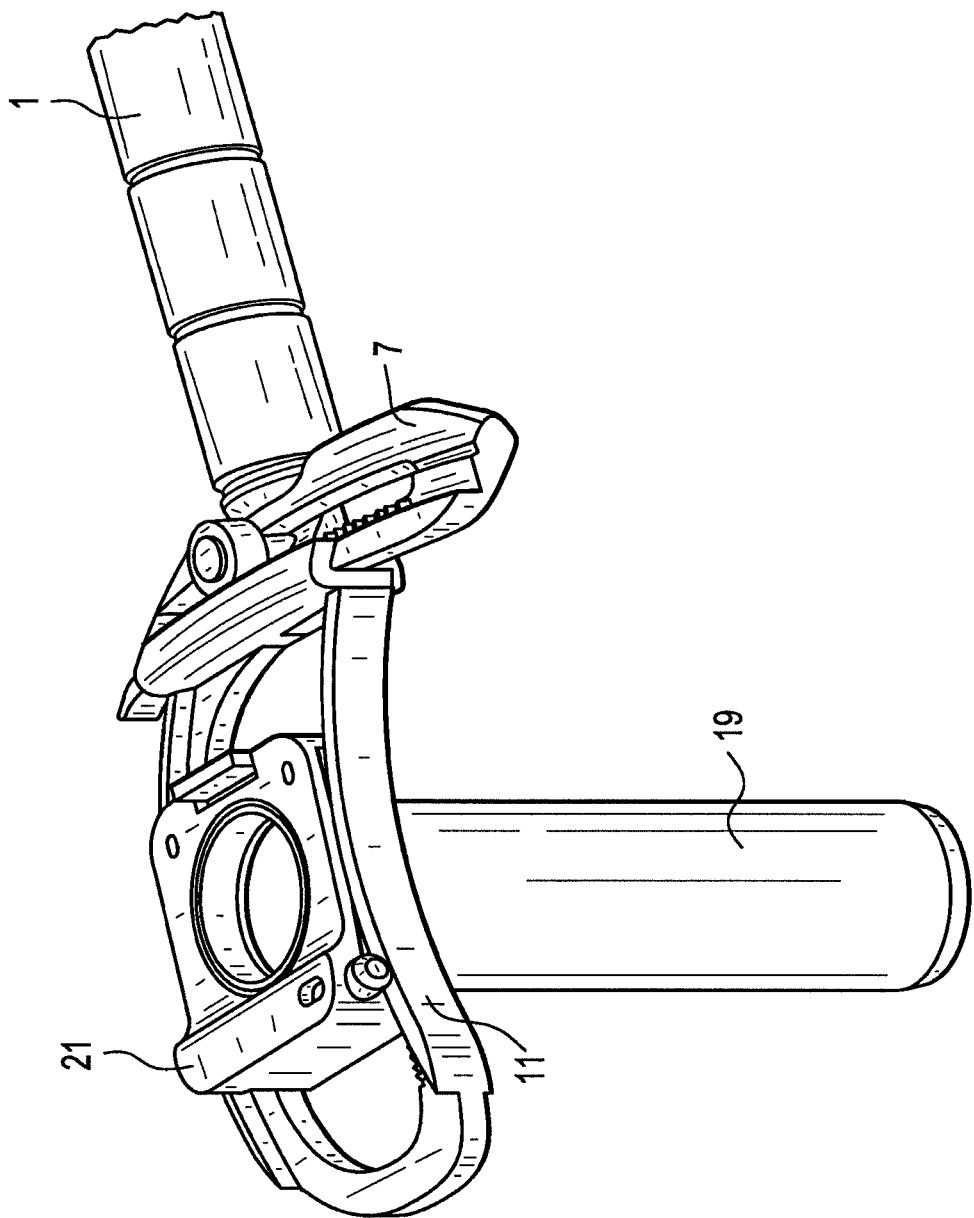

In FIG. 6C, the medial-lateral bar is attached to a rigid arm, whose position can be fixed relative to the operating room table during the surgery.

Although the cranial-caudal bar is shown in FIG. 6A as having four rails forming a rectangle with an internal window, in some embodiments, the cranial-caudal bar could potentially consist of 3 rails (defining a "U"-Shape) or 2 rails (defining an "L-" shape). Although the described "4-rail" configuration likely provides for the highest stability of these embodiments against bending of the working channel construct around the axis along the bar, and can provide for the finest dimensions of the rails at the same time, an very stiff sliding/connection mechanism that only needs support from one rail, or without the stabilization of the closing-rod, can also be considered as well.

In some embodiments (as in FIG. 6B), the cranial-caudal bar has a release button 25 for releasable attachment to the medial-lateral bar. Typically, pressing this button releases the engagement of a teeth-like element on the cranial-caudal bar within the tee engages the teeth of the rail of the medial-lateral bar.

In some embodiments (as in FIG. 6B), the slider has a release button 27 for releasable attachment to the cranial-caudal bar. Typically, this button engages the teeth of the second rail of the cranial-caudal bar.

In some embodiments (as in FIG. 6A), the medial-lateral bar has a first window 29 or slot therein for slidable reception of the cranial-caudal bar. Typically, the slot is adjacent the rail of the medial-lateral bar, and the first rail of the cranial-caudal bar has a bolt-like shape so as to provide a slidable bolt-slot connection with the medial-lateral bar.

In some embodiments (as in FIG. 6A), the cranial-caudal bar has a third rail 31 extending from the first rail of the cranial-caudal bar in a direction substantially parallel to the second rail of the cranial-caudal bar. This embodiment can provide a cranial-caudal bar having a U-shape. In this embodiment, stops can be provided at the two ends of the U-shape so that the slider remains within the pocket of the U-shape.

In some embodiments, the slider further comprises iii) a second rail (not shown) substantially parallel to the first rail of the slider, wherein the second rail of the slider is in slidable engagement with the third rail of the cranial-caudal bar.

In some embodiments (as in FIG. 6B), the tube is disposed between the second and third rails of the cranial-caudal bar. This allows the forces that act upon the tube to be evenly supported by the pair of rails of the cranial-caudal bar.

In some embodiments (as in FIG. 6A), a fourth rail (connecting bar) 35 connects the second and third rails of the cranial-caudal bar to form a second window 37, and the tube extends through the second window. This ensures that the slider will remain slidably attached to the cranial-caudal bar.

In some embodiments (as in FIG. 6B), the first rail of the medial-lateral bar and the first rail of the cranial-caudal bar have mating teeth 39 thereon, and the second rail of the cranial-caudal bar and the first rail of the working channel construct have mating teeth 41 thereon. With the help of a member that is integrated to the component that is sliding along the rail with the teeth, and that can engage the teeth, this allows the relative positions of the components to be fixed, thereby insuring the location of the working channel tube relative to the patient.

In some embodiments, a medical device is located within the tube. In some embodiments, thereof, the medical device is an instrument, while in others the medical device is an implant. Typically, the medical device is passed from the proximal end portion of the tube to the distal end portion of the working tube.

In some embodiments, the first rail of the medial-lateral bar and the first rail of the cranial-caudal bar have matching arcuate shapes. This allows the tube to be tilted with respect to the patient in a first plane while maintaining the location of the distal end of the tube.

In some embodiments, the second rail of the cranial-caudal bar and the first rail of the slider have matching arcuate shapes. This allows the tube to be tilted with respect to the patient in a second plane while maintaining the location of the distal end of the tube.

In some embodiments, the slider is attachable and detachable from/to the outer surface of the tube at the proximal end portion of the tube. This allows a fine control of the location of the proximal end portion of the tube. This allows as well that the tube can be introduced into the patient at the right location in a first step of a surgery. The rest of the components are pre-assembled and can be attached to the tube at this attachment location of the slider, while the arm is in a flexible configuration. After attaching the tube to the rest of the assembly, the arm can be brought to a rigid configuration, leaving only the option of changing the position of the tube, with respect to the patient to the angular changes by the rail connections.

Figure 6K:
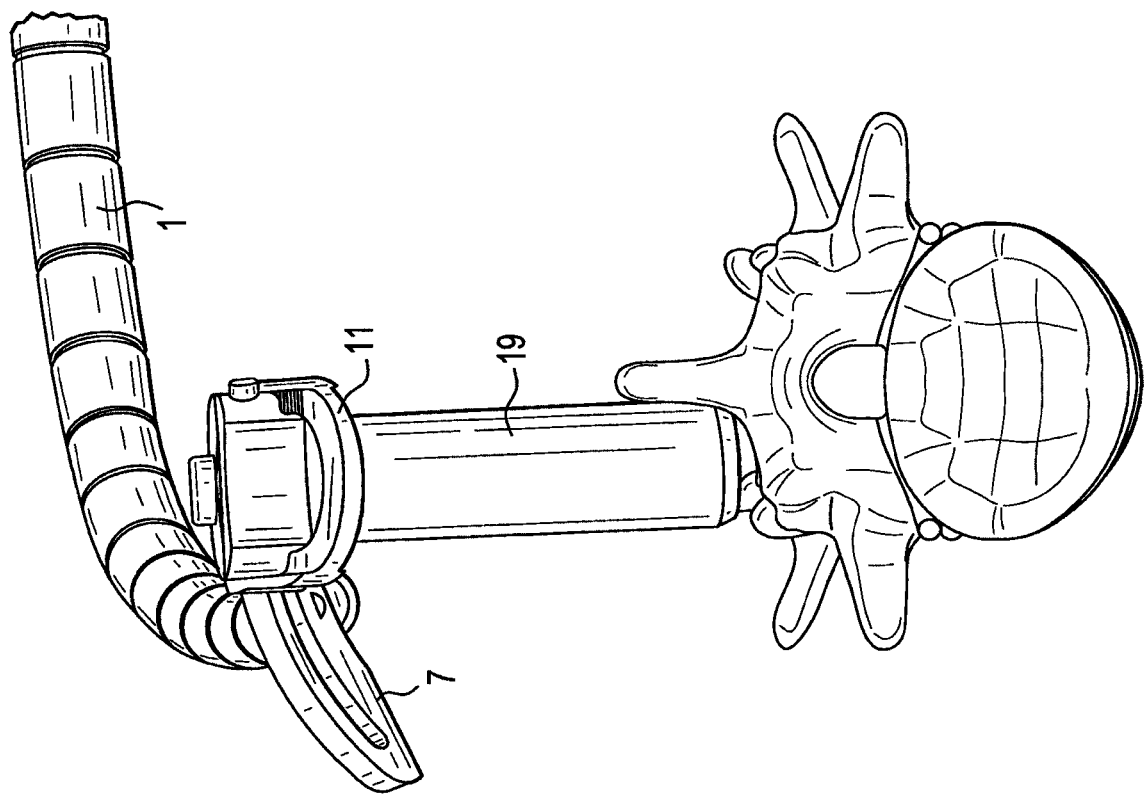
Figure 6L:
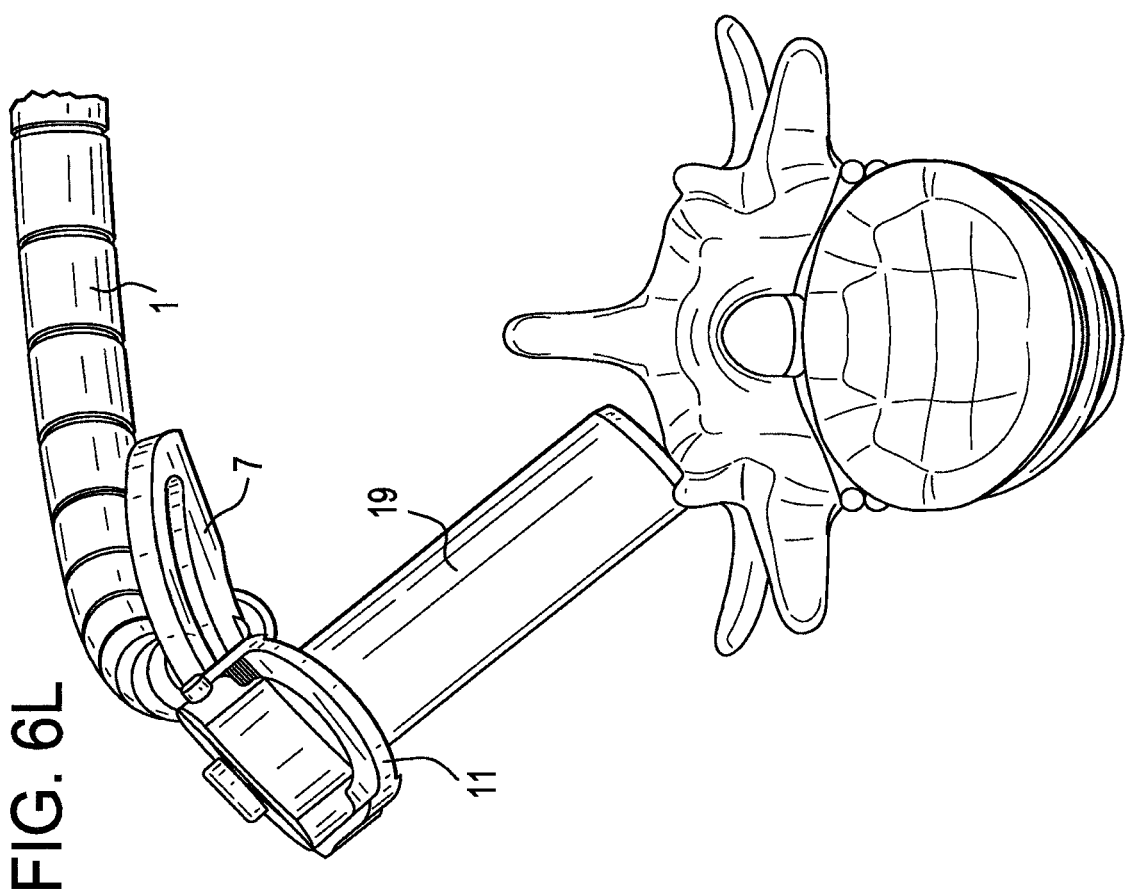
Figure 60:
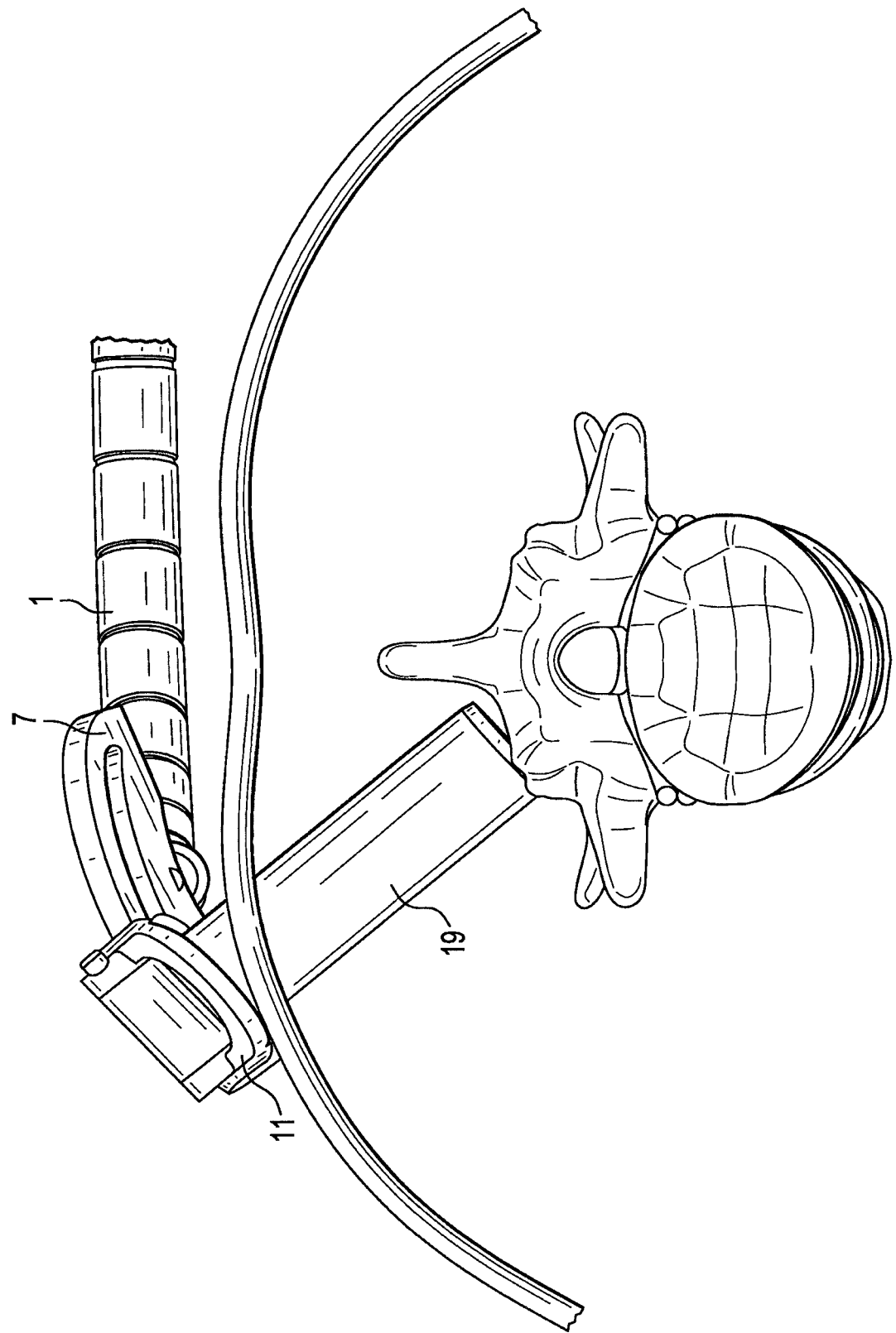
Figure 6P:
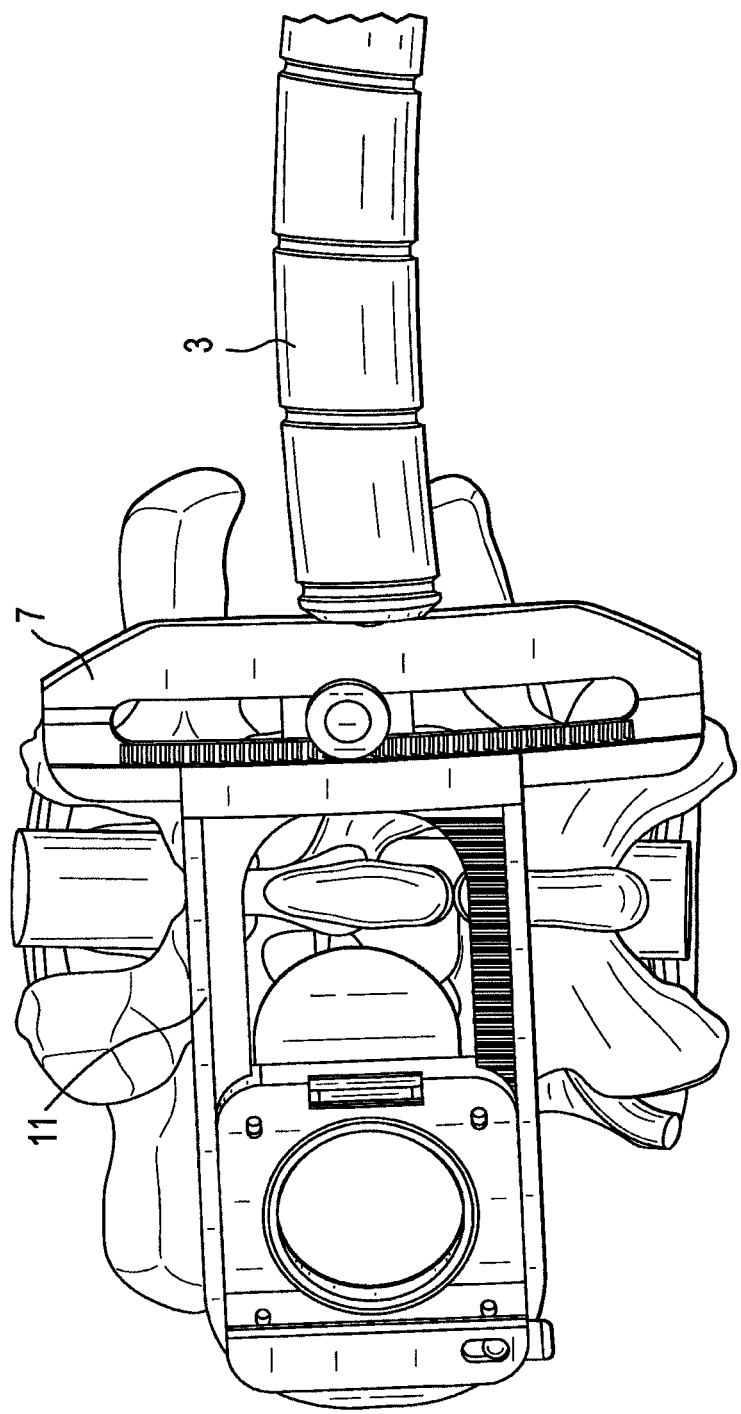

In some embodiments, the first rail of the cranial-caudal is in slidable engagement with the first rail of the medial-lateral bar by virtue of a bolt-slot connection. This arrangement helps maintain the orientation of the cranial-caudal bar vis-a-vis the medial-lateral bar. FIGS. 6K-6L disclose views of the fourth embodiment apparatus wherein the medial-lateral bar runs parallel to the spine.

The components of the present invention are preferably made from a biocompatible metal such as stainless steel, titanium alloy or cobalt-chrome. However, it is contemplated that the components can be made from polymeric materials so as to provide an inexpensive, single use system.

We claim:

1. An apparatus comprising:
   an arm having a proximal end portion connected to a stationary object and a distal end portion;
   a first bar connected to the distal end portion of the arm and having an arcuate rail;
   a second bar cantilevered from the first bar and having:
     a first arcuate rail in slidable engagement with the arcuate rail of the first bar in a first direction, and
     a second arcuate rail extending substantially perpendicularly from the first arcuate rail of the second bar;
   a working channel construct comprising:
     a tube having an outer surface and a proximal end portion and a distal end portion, and
     a slider attached to the outer surface of the tube and having a first arcuate rail in slidable engagement with the second arcuate rail of the second bar in a second direction,
   wherein the first arcuate rail of the second bar is configured to slide to a position along the arcuate rail of the first bar to configure a first tilt angle of the proximal end portion of the tube in a first plane while maintaining a location of the distal end portion of the tube; and
   wherein the first arcuate rail of the slider is configured to slide to a position along the second arcuate rail of the second bar to configure a second tilt angle of the proximal end portion of the tube in a second plane while maintaining the location of the distal end portion of the tube,
   wherein the second bar has a third arcuate rail extending from the first arcuate rail of the second bar in a direction substantially parallel to the second arcuate rail of the second bar with the tube disposed between the second and third arcuate rails, and
   wherein the second and third arcuate rails form a window through which the tube extends.

2. The apparatus of claim 1 wherein the second bar has a release button for releasable attachment to the first bar.

3. The apparatus of claim 1 wherein the slider has a release mechanism for releasable attachment to the second bar.

4. The apparatus of claim 1 wherein the first bar has a first window therein for slidable reception of the second bar.

5. The apparatus of claim 1 wherein the slider further having a second arcuate rail substantially parallel to the first arcuate rail of the slider, wherein the second arcuate rail of the slider is in slidable engagement with the third arcuate rail of the second bar.

6. The apparatus of claim 1 wherein a fourth rail connects the second and third arcuate rails of the second bar to form the window.

7. The apparatus of claim 1 wherein the arcuate rail of the first bar and the first arcuate rail of the second bar have mating teeth thereon.

8. The apparatus of claim 1 wherein the second arcuate rail of the second bar and the first arcuate rail of the slider have mating teeth thereon.

9. The apparatus of claim 1 further comprising:
   a medical device located within the tube.

10. The apparatus of claim 9 wherein the medical device is an instrument.

11. The apparatus of claim 9 wherein the medical device is an implant.

12. The apparatus of claim 1 wherein the arcuate rail of the first bar and the first arcuate rail of the second bar have matching arcuate shapes.

13. The apparatus of claim 1 wherein the second arcuate rail of the second bar and the first arcuate rail of the slider have matching arcuate shapes.

14. The apparatus of claim 1 wherein the slider is attached to the outer surface of the tube at the proximal end portion of the tube.

15. The apparatus of claim 1 wherein the outer surface of the tube at the proximal end portion of the tube has a thread thereon, the slider has a window having a matching thread thereon, and the slider is threadably engaged with the proximal end portion of the tube.

16. The apparatus of claim 1 wherein the first arcuate rail of the second bar is in slidable engagement with the arcuate rail of the first bar by virtue of a bolt-slot connection.

17. The apparatus of claim 1, wherein the first tilt angle is a medial-lateral tilt angle and the second tilt angle is a cranial-caudal tilt angle.

* * * * *